(12) United States Patent
Masuda et al.

(10) Patent No.: US 11,733,131 B2
(45) Date of Patent: Aug. 22, 2023

(54) TISSUE SLICE SELECTION METHOD, AND EMBEDDED BLOCK PREPARING CASSETTE

(71) Applicants: NIHON UNIVERSITY, Tokyo (JP); NICHIREI BIOSCIENCES INC., Tokyo (JP)

(72) Inventors: Shinobu Masuda, Tokyo (JP); Ryohei Suzuki, Tokyo (JP); Yuriko Kitano, Higashimurayama (JP)

(73) Assignees: NIHON UNIVERSITY, Tokyo (JP); NICHIREI BIOSCIENCES INC., Tokyo (JP)

(*) Notice: Subject to any disclaimer, the term of this patent is extended or adjusted under 35 U.S.C. 154(b) by 859 days.

(21) Appl. No.: 16/609,074

(22) PCT Filed: Apr. 27, 2018

(86) PCT No.: PCT/JP2018/017336
§ 371 (c)(1),
(2) Date: Oct. 28, 2019

(87) PCT Pub. No.: WO2018/199335
PCT Pub. Date: Nov. 1, 2018

(65) Prior Publication Data
US 2020/0149999 A1 May 14, 2020

(30) Foreign Application Priority Data

Apr. 28, 2017 (JP) ................................ 2017-090793

(51) Int. Cl.
| | | |
|---|---|---|
| *G01N 1/06* | (2006.01) | |
| *G01N 1/30* | (2006.01) | |
| *G01N 1/36* | (2006.01) | |
| *G01N 33/52* | (2006.01) | |

(52) U.S. Cl.
CPC ................. *G01N 1/06* (2013.01); *G01N 1/30* (2013.01); *G01N 1/36* (2013.01); *G01N 33/52* (2013.01)

(58) Field of Classification Search
CPC .. G01N 1/06; G01N 1/30; G01N 1/36; G01N 33/52; G01N 33/531
See application file for complete search history.

(56) References Cited

U.S. PATENT DOCUMENTS

| 4,893,424 A | 1/1990 | McLean | |
|---|---|---|---|
| 5,610,022 A * | 3/1997 | Battifora | G01N 33/743 |
| | | | 436/63 |
| 6,406,840 B1 | 6/2002 | Li et al. | |
| 2006/0051736 A1* | 3/2006 | Shields | G01N 1/30 |
| | | | 435/40.5 |
| 2006/0269985 A1 | 11/2006 | Kitayama | |
| 2007/0037138 A1 | 2/2007 | Winther | |
| 2016/0274008 A1 | 9/2016 | Chen et al. | |

FOREIGN PATENT DOCUMENTS

| JP | 61-502560 A | 11/1986 | |
|---|---|---|---|
| JP | 8-035921 A | 2/1996 | |
| JP | 2006-519376 A | 8/2006 | |
| JP | 4013192 B2 | 11/2007 | |
| JP | 4758672 B2 | 8/2011 | |
| JP | 2014202725 A * | 10/2014 | ............... G01N 1/36 |
| JP | 2015-129739 A | 7/2015 | |
| JP | 2015-155873 A | 8/2015 | |
| JP | 2016-520814 A | 7/2016 | |

OTHER PUBLICATIONS

International Search Report (PCT/ISA/210) issued in PCT/JP2018/017336, dated Jul. 17, 2018.
Nichirei Biosciences Inc. "HER2 Inspection Determination Method", [online], Search on Apr. 3, 2018, Internet (URL:http://www.nichirei.co.jp/bio/technical/protocol/her2/judge.html).
Nichirei Biosciences Inc. "Histofine HER2 kit (MONO) Operation Procedure", [online], Search on Apr. 3, 2018, Internet (URL:http://www.nichirei.co.jp/bio/technical/protocol/her2/mono03.html).
Written Opinion (PCT/ISA/237) issued in PCT/JP2018/017336, dated Jul. 17, 2018.
Extended European Search Report for European Application No. 18791808.1, dated Dec. 3, 2020.

* cited by examiner

*Primary Examiner* — Lynn Y Fan

(74) *Attorney, Agent, or Firm* — Birch, Stewart, Kolasch & Birch, LLP

(57) ABSTRACT

The present invention is to provide a tissue slice selection method and an embedded block-preparing cassette which are capable of suppressing occurrence of errors in inspection results. The present invention makes it possible to suppress the occurrence of errors in inspection results by including: an embedded block-preparing process of preparing an embedded block by embedding both a biological tissue fragment and a standard substance in the same embedding agent; an embedded tissue slice preparing step of slicing the embedded block to prepare a sheet-like embedded tissue slice having a tissue slice and standard substance slices appearing on a surface thereof; and a tissue slice selecting step of selecting the tissue slice to be inspected, based on a light signal from the standard substance slice.

6 Claims, 15 Drawing Sheets

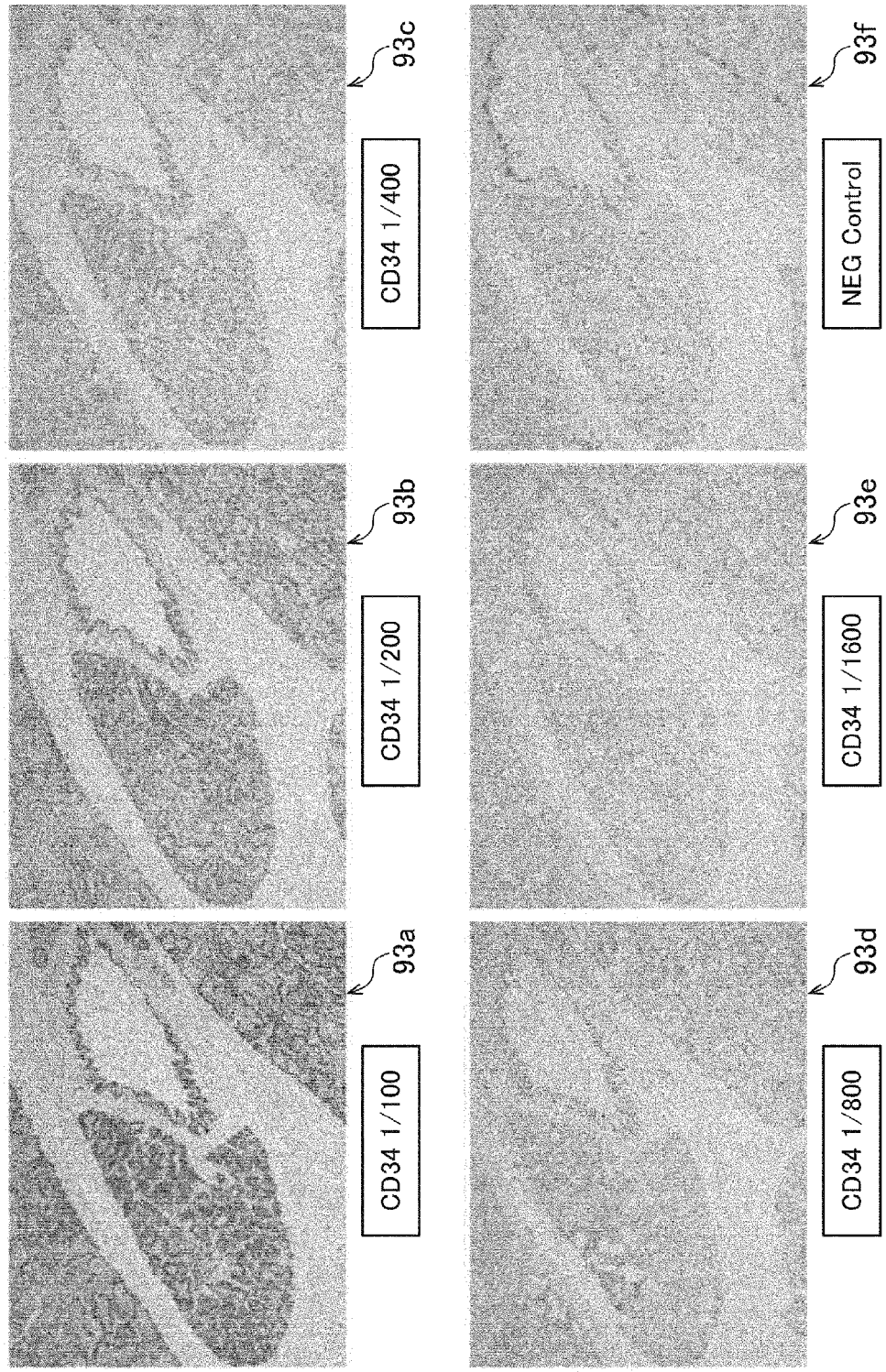

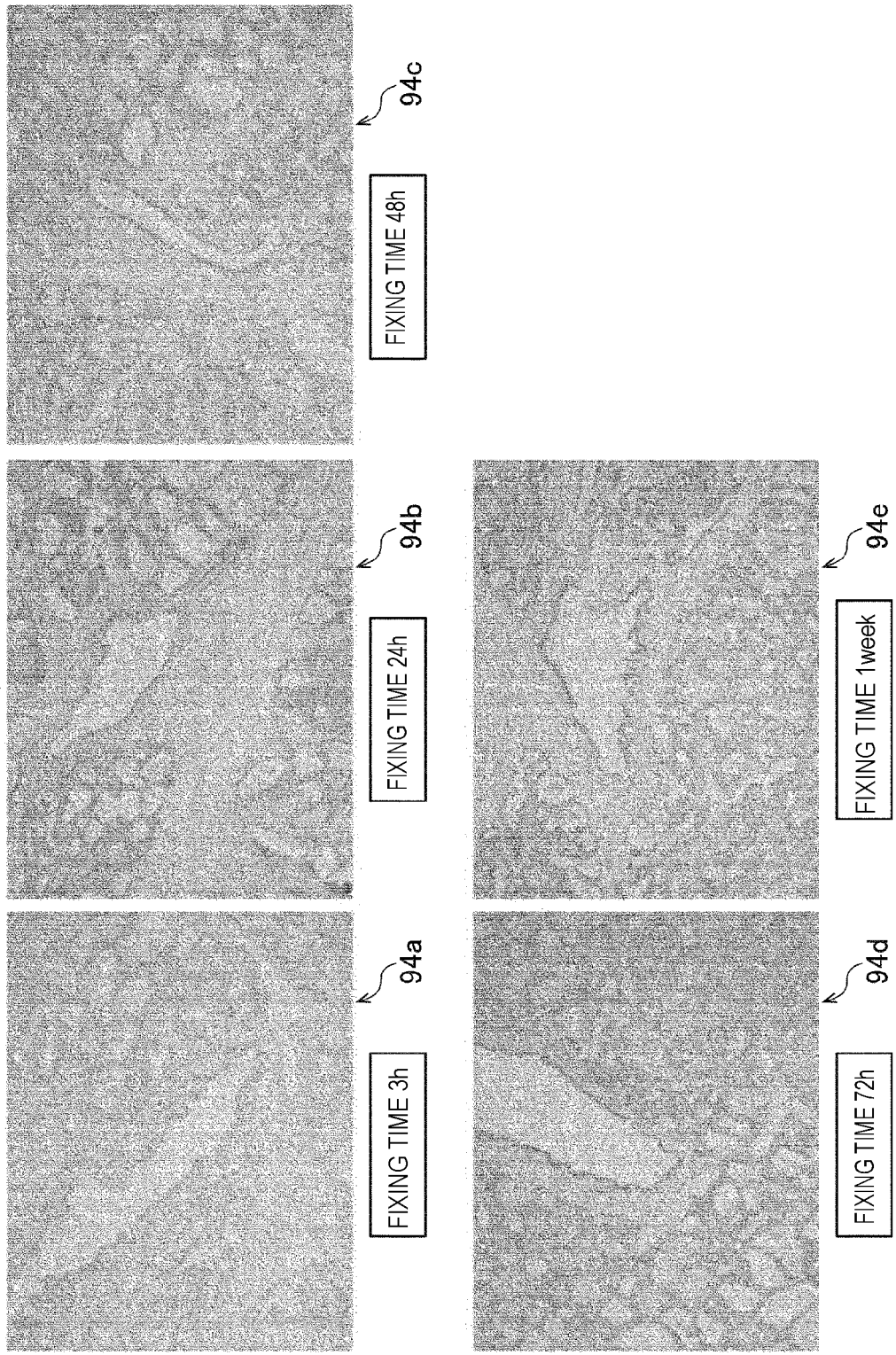

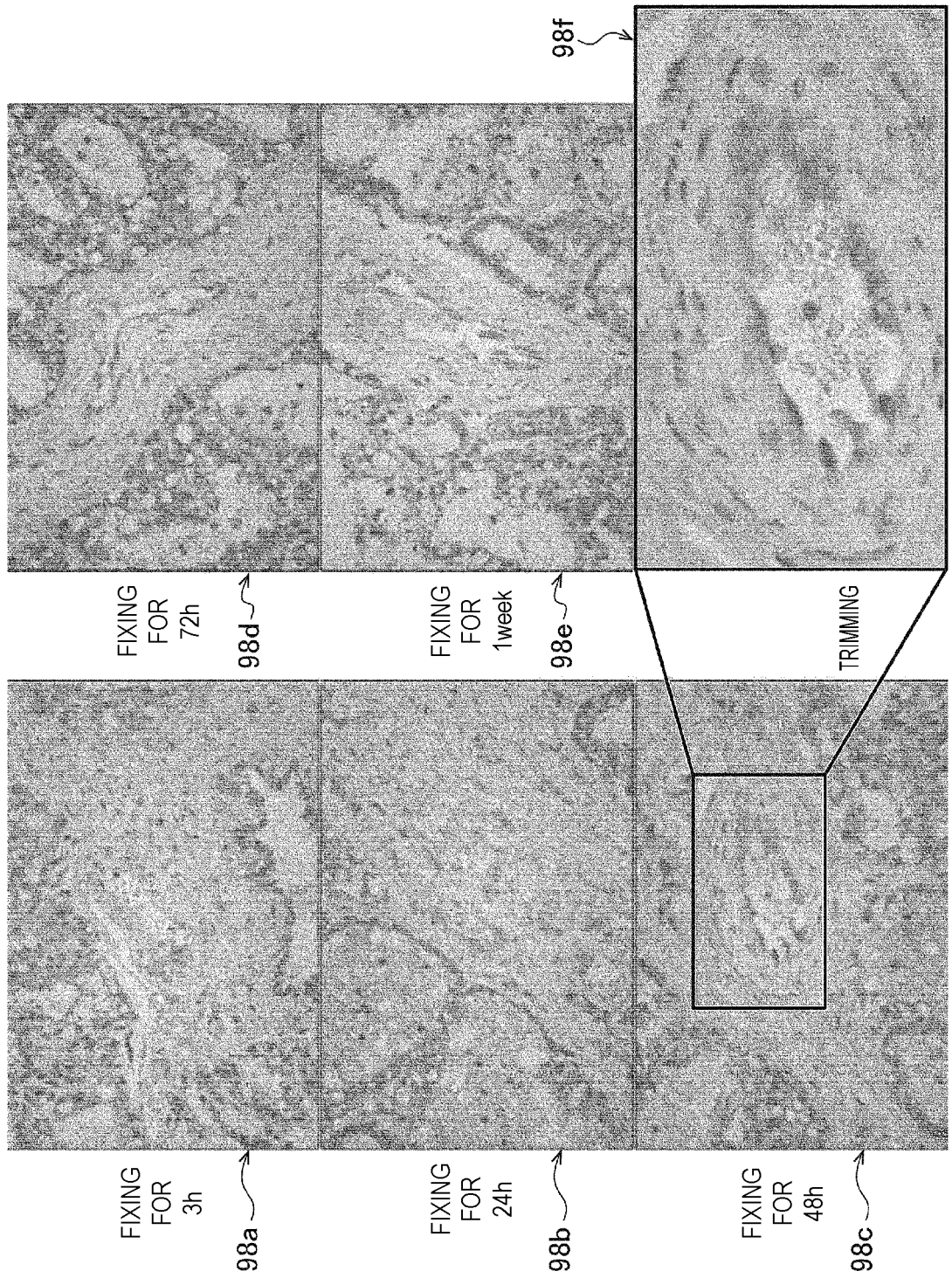

TISSUE SLICE SELECTION METHOD, AND EMBEDDED BLOCK PREPARING CASSETTE

TECHNICAL FIELD

The present invention relates to a tissue section selection method and an embedded block-preparing cassette.

BACKGROUND ART

It is known that in a cancer tissue, specific genes are amplified and proteins, the products of the genes, are over-expressed. In the inspection of cancer and the like, over-expression of the protein or gene amplification in a specimen obtained from a living body is detected by an immunohistochemical staining method, and the condition of the specimen is inspected.

For example, HER2/neu protein, which is a gene product of an HER2/neu gene, is over-expressed with a high frequency in tumor cells such as breast cancer, the HER2/neu gene being one of oncogenes. Therefore, it is possible to inspect whether a subject suffers from cancer by detecting the HER2/neu protein in tumor cells using the immunohistochemical staining method and determining the presence or absence of over-expression of the HER2/neu protein.

As an inspection kit to which such principle is applied, commercially available is an immunohistochemical staining kit using an anti-human HER2/neu gene product monoclonal antibody (SV2-61γ) (animal species: mouse) that targets the HER2/neu protein expressed in the tumor cells and recognizes an extracellular region of the HER2/neu protein.

In such immunohistochemical staining kit, a specimen is immunohistochemically stained (hereinafter, simply referred to as stained) through the following steps. First, for example, a specimen is prepared in a stainable format through a provision step of providing an embedded block in which a biological tissue fragment collected from a human is embedded in an embedding agent such as paraffin, a preparation step of slicing the embedded block to a desired thickness using a microtome to prepare a sheet-like embedded tissue section in which a periphery of the tissue section is surrounded by an embedding agent section, and a placing step of placing the embedded tissue section prepared in this manner on a slide glass.

Subsequently, a deparaffinization treatment step of removing paraffin from the embedded tissue section on the slide glass and an antigen retrieval treatment step of activating the tissue section are performed.

Finally, performed are a blocking treatment step such as an endogenous peroxidase treatment with 3 V/V % peroxide, a primary antibody reaction treatment step in which a primary antibody is bound to a specific antigen in the tissue section, a secondary antibody reaction treatment step in which a secondary antibody bound to a labeled enzyme is bound to the primary antibody, and a staining treatment step in which the specific antigen in the tissue section is stained by using chromogenic development with a substrate solution containing a chromogenic substrate (for example, DAB: 3,3'-diaminobenzidine). The tissue section is stained through such a series of steps (NTL 1).

At this time, a control slide for determining suitability of the staining is provided separately from the embedded tissue section, and the tissue section and the control slide are stained at the same time. The control slide has a specimen sample, and thus can determine the suitability of the staining from the staining intensity of the specimen sample. If it is confirmed that the staining has been suitably performed from the control slide, a staining intensity score of the tissue section is determined based on predetermined criteria, and from the result of the score determination (evaluation), the presence or absence of a lesion tissue in the tissue section is determined (NTL 2).

CITATION LIST

Non Patent Literature

Non Patent Literature 1: NICHIREI BIOSCIENCES INC. "Histofine HER2 kit (MONO) Operation Procedure", [online], Search on Apr. 3, 2018, Internet (URL:http://www.nichirei.co.jp/bio/technical/protocol/her2/mono03.html)

Non Patent Literature 2: NICHIREI BIOSCIENCES INC. "HER2 Inspection Determination Method", [online], Search on Apr. 3, 2018, Internet (URL:http://www.nichirei.co.jp/bio/technical/protocol/her2/judge.html)

SUMMARY OF INVENTION

Technical Problem

A tissue section for inspection using such immunohistochemical staining is usually prepared by slicing an embedded block to a thickness of several micrometers using an instrument such as a microtome, as described above. In the slicing operation using the microtome, a variance in thickness may occur depending on a skill level of the engineer, a preparation environment (for example, room temperature and humidity), and a type of embedded tissue, and the manipulation deviation may occur even by the same engineer and thus a variance in thickness may occur.

In the inspection using the immunohistochemical staining, since the staining intensity changes depending on the thickness of the tissue section, variance in the thickness of the tissue section has a large influence on the inspection result. For example, when a variance occurs in the thickness of multiple tissue sections used for the inspection, the tissue sections will not exhibit the same staining intensity and will have a different staining intensity depending on the thickness of the tissue section even when the staining is simultaneously performed under the same conditions. Therefore, when there is a variance in thickness of the tissue sections, a score which is different from the state of the actual tissue section may be determined, which may cause an error in the inspection result.

In the inspection using the immunohistochemical staining, furthermore, suitability of the staining is determined using a control slide provided separately from the embedded tissue section to improve the accuracy of the inspection result. However, even in this case, there is a demand for improving the accuracy of the inspection result by suppressing occurrence of an error in the inspection result.

Furthermore, before the embedded block is prepared, a fixing treatment, for example, is performed, in which the biological tissue fragment is immersed in a fixing solution such as a formalin aqueous solution for a predetermined period of time to appropriately fix the tissue form and/or the antigen activity of the biological tissue fragment. However, when the fixing time is not appropriate during the fixing treatment and/or the biological tissue fragment is not appropriately fixed, the tissue form and/or the antigen activity of the biological tissue fragment may not be maintained, and thereafter, an error may occur in the inspection result during the inspection of the tissue section.

The present invention has been made in view of the above problems, and an object thereof is to provide a tissue section selection method and an embedded block-preparing cassette which can suppress occurrence of an error in the inspection result.

Solution to Problem

A tissue section selection method of the present invention is a tissue section selection method of selecting a tissue section to be inspected by specifically detecting a marker, which comprises: an embedded block-preparing step for preparing an embedded block by embedding both a biological tissue fragment and a standard substance in the same embedding agent; an embedded tissue section-preparing step of slicing the embedded block for preparing a sheet-like embedded tissue section having the tissue section and a standard substance section appearing on a surface thereof; and a tissue section selecting step for selecting the tissue section to be inspected, based on a light signal from the standard substance section. In the present application, the light signal means an optically detectable signal, for example, a reflected light from the surface of the standard substance section.

The embedded block-preparing cassette of the present invention is an embedded block-preparing cassette used for preparing an embedded block in which a biological tissue fragment is embedded, and includes a box body that is placed on a tray into which a liquid embedding agent is poured. The box body includes: a frame having a through hole which penetrates an upper surface and a lower surface in a region facing the biological tissue fragment on the bottom of the tray; and a standard substance-positioning portion that is provided to face the bottom of the tray and has a positioning hole into which a standard substance is inserted, wherein the standard substance-positioning portion allows the standard substance to be positioned such that the standard substance is present within a height ranging from a lower end to an upper end of the biological tissue fragment when the bottom of the tray is taken as a reference.

A tissue section selection method of the present invention is a tissue section selection method of selecting a tissue section to be inspected by specifically detecting a marker, which comprises: an embedded block-preparing step of, after immersing a biological tissue fragment in a fixing solution for a predetermined period of time, preparing an embedded block by embedding the biological tissue fragment in an embedding agent; an embedded tissue section-preparing step of slicing the embedded block to prepare a sheet-like embedded tissue section having the tissue section appearing on a surface thereof; and a fixing state determining step of performing a staining treatment on the embedded tissue section and determining a fixing state of the tissue section fixed with the fixing solution based on a light signal from an endogenous protein expressed in cells in the tissue section.

Advantageous Effect of Invention

In the tissue section selection method of the present invention, the tissue section to be inspected is selected based on the light signal from the standard substance section, using the sheet-like embedded tissue section in which the tissue section and the standard substance section appear on the same surface. Thus, the inspection can be performed only on the tissue section optimal for the inspection in the tissue section selection method, and thus it is possible to suppress occurrence of an error in the inspection result.

In the embedded block-preparing cassette of the present invention, since the embedded block is prepared by embedding both the biological tissue fragment and the standard substance in the same embedding agent, it is possible to prepare an embedded tissue section in which the tissue section and the standard substance section appear on the same surface when the embedded block is sliced. Thus, in the embedded block-preparing cassette, the tissue section to be inspected can be selected based on a light signal from the standard substance section, and inspection can be performed only on the tissue section optimal for the inspection. Thus, it is possible to suppress occurrence of an error in the inspection result.

Since the tissue section selection method of the present invention enables evaluation of the fixing state of the tissue section fixed with the fixing solution, inspection can be performed only on the tissue section in a fixing state optimal for the inspection, and occurrence of an error in the inspection result can be suppressed.

BRIEF DESCRIPTION OF DRAWINGS

FIG. 4 is a perspective view illustrating a configuration of an embedded block prepared using the embedded block-preparing cassette of the present invention.

FIG. 7 is a schematic view illustrating an upper configuration of an embedded block-preparing cassette of a modification example; wherein

FIG. 8 is a schematic view illustrating an upper configuration of an embedded block-preparing cassette of a modification example; wherein

FIG. 16 shows photographs illustrating images obtained when examining a concentration of an anti-CD34 rabbit polyclonal antibody.

FIG. 17 shows photographs illustrating images obtained when verification was performed using a tissue block immersed in a fixing solution immediately after excision from a porcine mammary gland tissue, and an antibody having a concentration of 1/400.

FIG. 18 shows photographs illustrating an example of image used for preparing the graph illustrated in FIG. 15.

DESCRIPTION OF EMBODIMENTS

(1) Outline of Embedded Block-preparing Cassette of Present Invention

Figure 1:
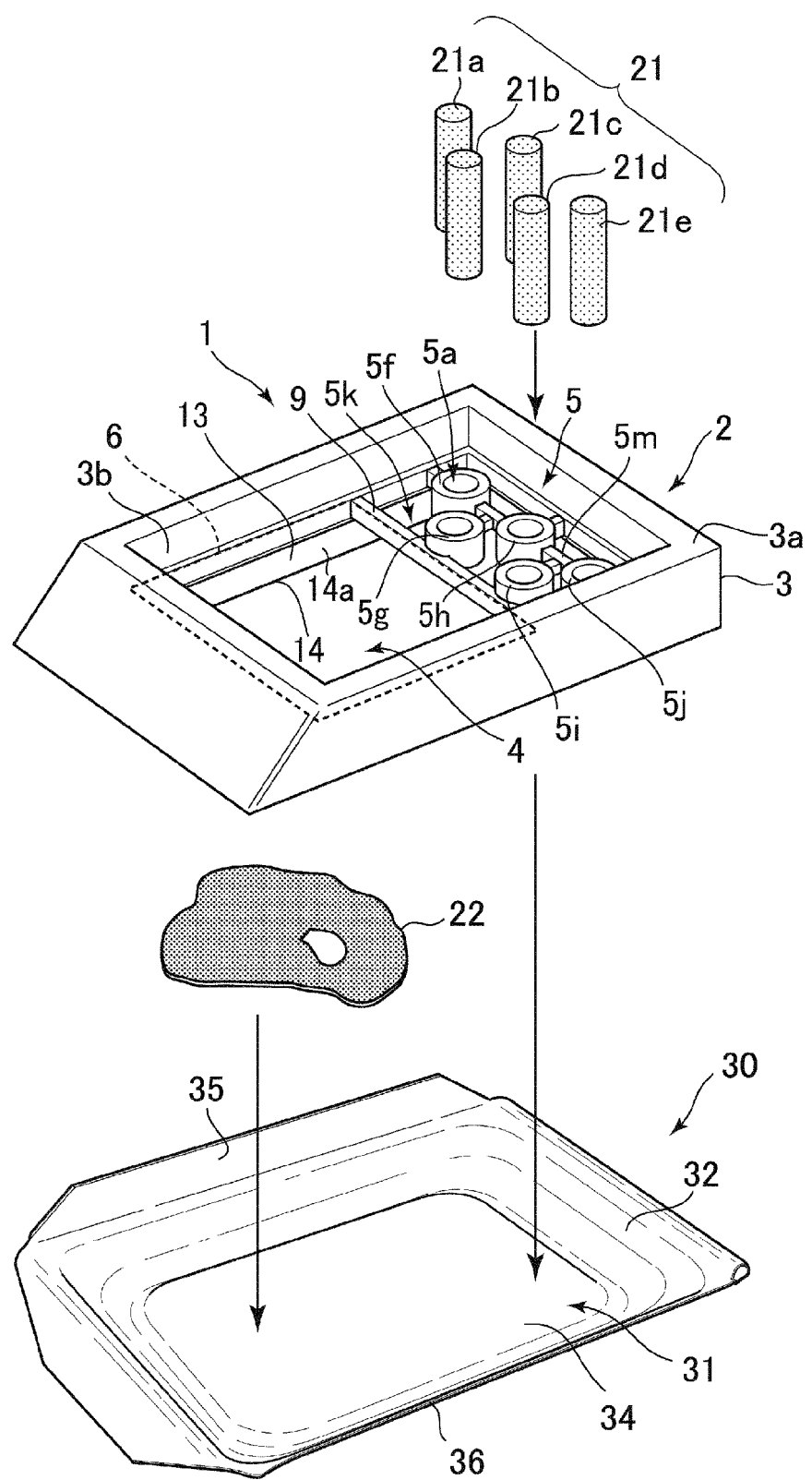
FIG. 1 is a schematic view illustrating an overall configuration and usage of an embedded block-preparing cassette of the present invention.

As illustrated in FIG. 1, an embedded block-preparing cassette 1 according to an embodiment of the present invention is used in a state of being placed on a tray 30, and is a tool for embedding both a standard substance 21 and a biological tissue fragment 22 in the same embedding agent to prepare an embedded block (which will be described later). The embedding agent (not illustrated) is a material such as paraffin that liquefies when heated and solidifies again when cooled. The embedded block-preparing cassette 1 is mounted on a slicing instrument, such as a microtome, when the embedded block is sliced. Therefore, the shape and size of the embedded block-preparing cassette 1 are appropriately selected according to the slicing instrument to be used.

Hereinafter, an embedded block-preparing cassette 1 will be described by way of a case where the embedded block used for an immunohistochemical staining method is prepared as an example. Further, explained herein is a case in which HER2/neu protein is used as a marker contained in a biological tissue and an immunohistochemical staining method for specifically detecting the HER2/neu protein to inspect a state of a living body is performed.

The embedded block-preparing cassette 1 is made of a synthetic resin material, such as plastic, phenolic resin, melamine resin, or polystyrene, and includes a box body 2 having an outer shape formed to conform to a mounting part of the slicing instrument. A frame 3 is formed in the box body 2 so as to surround an opening 4 that penetrates from an upper surface 3a to a lower surface. In the case of this embodiment, the frame 3 is formed into a truncated pyramidal shape in which one side surface of a rectangular parallelepiped is inclined, and the opening 4 is formed into a quadrilateral shape.

A standard substance-positioning portion 5 and a through hole 6 are provided in a region in the opening 4 surrounded by the frame 3. When the embedded block-preparing cassette 1 is placed on the tray 30, the standard substance-positioning portion 5 is provided in a predetermined region of the opening 4 so as to keep away from the biological tissue fragment 22 placed on a bottom surface 34 of the tray 30 (hereinafter, simply referred to as a tray bottom) and face the tray bottom 34. The standard substance-positioning portion 5 is provided with a plurality of positioning holes 5a, to which standard substances 21 (which will be described later) are respectively inserted. When the embedded block-preparing cassette 1 is placed on the tray 30, the standard substance-positioning portion 5 causes the standard substances 21 to be located so as to be kept away from the biological tissue fragment 22 placed on the tray bottom 34. Accordingly, the standard substances 21 are disposed to be aligned with the biological tissue fragment 22 on the tray bottom 34 by the standard substance-positioning portion 5.

A through hole 6 is provided in the remaining region other than the region in which the standard-positioning portion 5 is provided in the opening 4. The through hole 6 penetrates the upper surface 3a and the lower surface, and when the embedded block-preparing cassette 1 is placed on the tray 30, the biological tissue fragment 22 placed on the tray bottom 34 can be exposed through the through hole 6 when seen from above.

The tray 30 includes an accommodating portion 31 that is recessed in a tray shape, a shoulder 32 that is provided along an outer circumference of the accommodating portion 31, and a pair of first flange portion 35 and second flange portion 36 provided around the outer circumference of the shoulder 32. In the accommodating portion 31, the biological tissue fragment 22 is placed on the tray bottom 34 in the accommodating portion 31 when an embedded block is to be prepared. In addition, the accommodating portion 31 accommodates a liquid embedding agent poured into the tray 30 after the embedded block-preparing cassette 1 is placed on the tray 30. The liquid embedding agent is cooled and solidified in the accommodating portion 31 in a state where the embedded block-preparing cassette 1 is placed on the tray 30.

The shoulder 32 abuts on the embedded block-preparing cassette 1 and supports the embedded block-preparing cassette 1. The first flange portion 35 and the second flange portion 36 are respectively provided on the two opposing sides of the shoulder 32, and guide the embedded block-preparing cassette 1 such that the embedded block-preparing cassette 1 is placed on the shoulder 32.

The standard substance 21 is formed in the same shape (columnar shape) as a hole shape (here, columnar shape) of each positioning hole 5a in the standard substance-positioning portion 5. The standard substance 21 refers to a thickness standard substance 21a that serves as a reference for the thickness of a tissue section which will be described later, and marker standard substances 21b, 21c, 21d and 21e that serve as a reference for the suitability of the marker detection results, and here, the thickness standard substance 21a and the marker standard substances 21b, 21c, 21d and 21e are collectively referred to as the standard substance 21. In the present embodiment, as described above, a case where the HER2/neu protein in the biological tissue is detected is taken as an example. An amount of HER2/neu protein in the living body is usually evaluated in four stages: 0 (negative), 1+, 2+, and 3+.

For this purpose, as a marker standard substance that serves as a reference for the suitability of the marker detection results, used are a marker standard substance 21$b$ made from a cell line MDA-MB-231 which shows negative staining result, a marker standard substance 21$c$ made from a cell line MDA-MB-175VII showing a staining result of 1+, a marker standard substance 21$d$ made from a cell line MDA-MB-453 showing a staining result of 2+, and a marker standard substance 21$e$ made from a cell line SK-BR-3 showing a staining result of 3+.

The marker standard substances 21$b$, 21$c$, 21$d$ and 21$e$ respectively are prepared by preparing control cell embedded blocks in which the above-described cell lines are embedded, and hollowing out the control cell embedded blocks into a columnar shape using BIOPSY PUNCH (manufactured by Kai Industries).

The thickness standard substance 21$a$ is made of a material of which color tone changes as an optical signal depending on the thickness. For example, a pigment-containing urethane foam prepared by mixing a pigment of a predetermined color, such as blue, can be used as a thickness standard substance 21$a$. The thickness standard substance 21$a$ is not particularly limited as long as the color information, such as the color tone, changes depending on the thickness.

In the present embodiment, the thickness standard substance 21$a$ is prepared by the following procedures. First, a blue pigment-containing urethane foam having a predetermined size (for example, 100 to 110 mm in length, 60 to 70 mm in width, 30 to 40 mm in height, and 35 to 45 g in weight) is prepared. The blue pigment-containing urethane foam is cut in a height direction with a width of approximately 5 mm such that a cutting surface is parallel to a lateral direction of the blue pigment-containing urethane foam. Subsequently, from the blue pigment-containing urethane foam cut into a sheet shape, the vicinity of the center where the number of bubbles contained in the blue pigment-containing urethane foam is small is excised, and the excised foam is further cut into a sheet shape with a thickness of approximately 5 mm, to prepare small urethane foam fragments.

The small urethane foam fragments are placed in a commercially available paraffin-embedded block-preparing cassette EB-W (manufactured by Olympus), and an immobilization treatment is performed using a closed type automatic immobilization embedding apparatus Tissue-Tek VIP (manufactured by Sakura Finetek Japan). The thickness standard substance 21$a$ is prepared by hollowing the small urethane foam fragments to which the immobilization treatment was performed and cut into a columnar shape by using tissue micro-array apparatus KIN-2 type (manufactured by Azumaya Medical Instruments Co., Ltd.).

(2) Detailed Configuration of Embedded Block-Preparing Cassette

Figure 2:
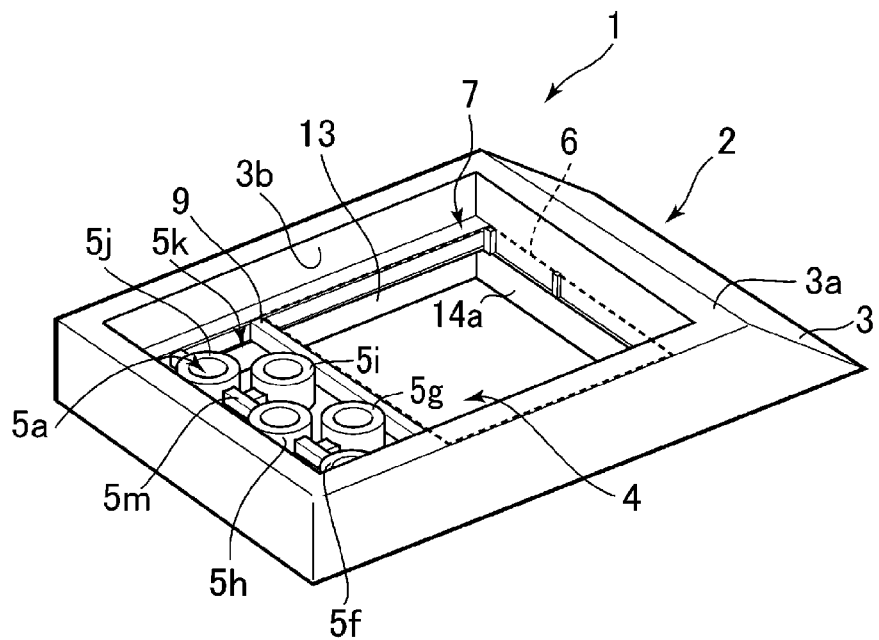
FIG. 2 is a perspective view illustrating an overall configuration (1) of the embedded block-preparing cassette of the present invention.

Here, in addition to FIG. 1, the embedded block-preparing cassette 1 will be described in more detail with reference to FIGS. 2 and 3 in which parts that correspond to those of FIG. 1 are given the same reference numerals. In the frame 3 provided in the box body 2, a square bar-like horizontal bar 9 is bridged between a pair of opposing inner walls 3$b$ among the inner walls 3$b$ that surround the inside of the opening 4. The horizontal bar 9 is provided on the same surface as a lower surface 3$f$ of the frame 3 and divides the inside of the opening 4 into two regions, one region being used as a region for forming the standard substance-positioning portion 5, and the other region being used as a region for forming the through hole 6.

The standard substance-positioning portion 5 is formed of the same material as the frame 3 and has a plurality of positioning hole-forming portions 5$f$, 5$g$, 5$h$, 5$i$ and 5$j$ having a cylindrical shape. The positioning hole-forming portions 5$f$, 5$g$, 5$h$, 5$i$ and 5$j$ are separated away with a predetermined distance. The adjacent positioning hole-forming portions 5$f$, 5$g$ and 5$h$ (5$h$, 5$i$, and 5$j$) are connected to each other by a square bar-like connecting portion 5$m$, and the positioning hole-forming portions 5$f$, 5$h$ and 5$j$ adjacent to the inner wall 3$b$ of the frame 3 are respectively connected to the inner wall 3$b$ by the square bar-like connecting portion 5$m$. The side surfaces of the positioning hole-forming portions 5$g$ and 5$i$ adjacent to the horizontal bar 9 are also connected to the horizontal bar 9. In the standard substance-positioning portion 5, the region other than the positioning hole-forming portions 5$f$, 5$g$, 5$h$, 5$i$ and 5$j$ and the connecting portion 5$m$ is an opening 5$k$ that penetrates the upper surface 3$a$ and the lower surface 3$f$.

In this embodiment, the positioning hole-forming portions 5$f$, 5$g$, 5$h$, 5$i$ and 5$j$ have the same configuration, and pillar-like hollow regions that penetrate from the upper surface 3$a$ to the lower surface 3$f$ serve as a positioning hole 5$a$, and the standard substance 21 can be inserted into the positioning hole 5$a$. In the present embodiment, since the thickness standard substance 21$a$ and the marker standard substances 21$b$, 21$c$, 21$d$ and 21$e$ are used as described above, the standard substance-positioning portion 5 is provided with five positioning holes 5$a$.

In the standard substance-positioning portion 5, the positioning hole-forming portions 5$f$, 5$g$, 5$h$, 5$i$ and 5$j$ are fixed to the inner wall 3$b$ of the frame 3 via the connecting portion 5$m$ or the horizontal bar 9, the opening 5$k$ is formed among the positioning hole-forming portions 5$f$, 5$g$, 5$h$, 5$i$ and 5$j$, and a liquid embedding agent can be poured into the tray bottom 34 from the opening 5$k$. Further, the horizontal bar 9 between the through hole 6 and the standard substance-positioning portion 5 is provided on the same surface as the lower surface 3$f$ of the frame 3. Thus, when the embedded block-preparing cassette 1 is placed on the tray 30, a gap can be formed between the tray bottom 34 and the horizontal bar 9, and the liquid embedding agent poured into the tray 30 may also flow between the region of the through hole 6 and the region of the standard substance-positioning portion 5.

Here, since all of the positioning hole-forming portions 5$f$, 5$g$, 5$h$, 5$i$ and 5$j$ have the same configuration, for example, the following description will be given by focusing on the positioning hole-forming portion 5$g$. The positioning hole-forming portion 5$g$ is fixed to the inner wall 3$b$ of the frame 3 with the connecting portion 5$m$ or the horizontal bar 9 interposed therebetween such that the positioning hole 5$a$ faces the tray bottom 34. The positioning hole forming portion 5$g$ is formed at a predetermined height, and when the standard substance 21 is inserted into the positioning hole 5$a$, the one end of the standard substance 21 is brought into contact with the tray bottom 34, and the longitudinal direction of the standard substance 21 can be maintained to face the vertical direction with respect to the tray bottom 34. Accordingly, the positioning hole-forming portion 5$g$ can position the standard substance 21 in a height range from a lower end to an upper end of the biological tissue fragment 22 with respect to the tray bottom 34 when the embedded block is prepared.

In the present embodiment, when the embedded block-preparing cassette 1 is placed on the tray 30 on which the biological tissue fragment 22 is placed on the tray bottom 34, the box body 2 is formed such that the entire biological tissue fragment 22 is exposed to the outside from the through hole 6. Accordingly, in a state where the embedded block-preparing cassette 1 is placed on the tray 30 with the biological tissue fragment 22 placed on the tray bottom 34, the biological tissue fragment 22 is moved on the tray bottom 34 through the through hole 6, and the position of the biological tissue fragment 22 can be adjusted or the biological tissue fragment 22 lifted up from the tray bottom 34 can be pressed against the tray bottom 34 when the liquid embedding agent is poured.

In the present embodiment, mentioned is a case where the size of the through hole 6 is larger than the biological tissue fragment 22 so that the entire biological tissue fragment 22 placed on the tray bottom 34 can be seen from above through the through hole 6. However, the present invention is not limited thereto. Examples of through holes according to another embodiment may have such size that the entire part between the opposing both end portions of the biological tissue fragment 22 can be seen from above through the through hole 6 or may have such size that ⅓ or more of the biological tissue fragment 22 can be seen from above through the through hole 6.

Figure 3:
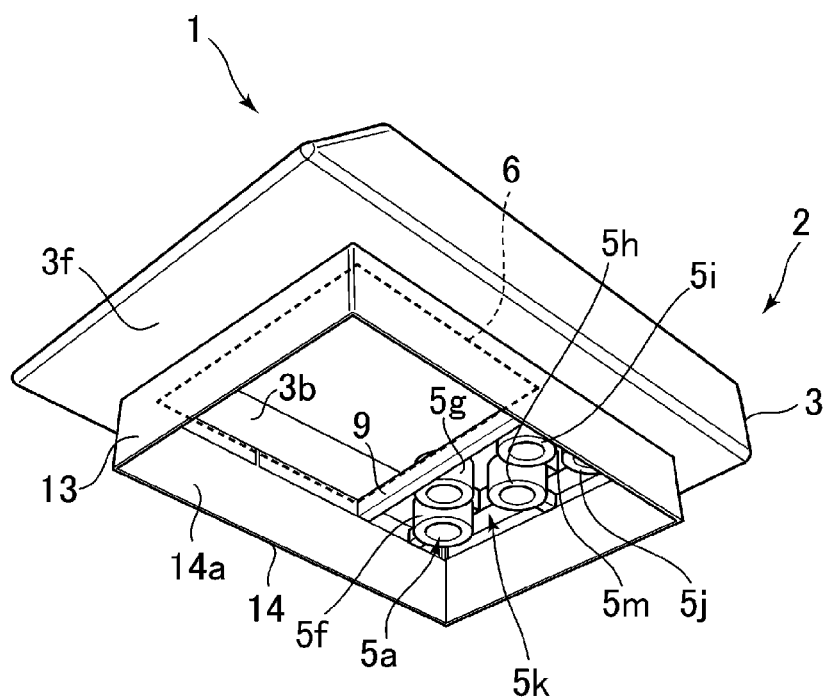
FIG. 3 is a perspective view illustrating an overall configuration (2) of the embedded block-preparing cassette of the present invention.

In addition to such a configuration, the box body 2 is provided with a plate frame portion 13 disposed in a quadrilateral shape on the lower surface 3f of the frame 3 as illustrated in FIG. 3. The plate frame portion 13 is provided such that an inner wall surface 14a surrounds the opening 4 of the frame 3. In other words, the plate frame portion 13 is provided so as to surround the formation region of the standard substance-positioning portion 5 and the formation region of the through hole 6 by the inner wall surface 14a.

When the box body 2 of the embedded block-preparing cassette 1 is placed on the shoulder 32 of the tray 30, the tip end 14 of the plate frame portion 13 abuts the bottom surface 34 of the tray 30, and a space surrounded by the tray bottom 34 and the inner wall surface 14a can be formed. Accordingly, when the embedded block-preparing cassette 1 is placed on the tray 30 and the liquid embedding agent is poured from the opening 4 to prepare an embedded block, the liquid embedding agent accumulates in the space surrounded by the tray bottom 34 and the plate frame portion 13, and the liquid embedding agent poured into the space flows between the region of the through hole 6 and the region of the standard substance-positioning portion 5. Thus, an embedded block in which both the standard substance 21 and the biological tissue fragment 22 are embedded in the same embedding agent can be prepared.

(3) How to Use Embedded Block-Preparing Cassette 1

Next, a usage of the embedded block-preparing cassette 1 will be described. The biological tissue fragment 22 obtained from a living body is placed at a predetermined position on the tray bottom 34 (mounting step). Next, the embedded block-preparing cassette 1 is placed on the tray 30 such that the lower surface 3f of the frame portion 3 of the embedded block-preparing cassette 1 is placed on the shoulder 32 of the tray 30. Thereby, the biological tissue fragment 22 on the tray bottom 34 is disposed in the region of the through hole 6 in the box body 2 of the embedded block-preparing cassette 1.

Subsequently, the standard substances 21 are inserted into each positioning hole 5a of the standard substance-positioning portion 5 one by one. At this time, the standard substances 21 are inserted into the positioning hole 5a until one end abuts on the tray bottom 34, and are respectively supported by the positioning hole-forming portions 5f, 5g, 5h, 5i and 5j. The standard substance 21 is placed up to the height of the biological tissue fragment 22. In the present embodiment, the thickness standard substance 21a is inserted into the positioning hole 5a of the positioning hole-forming portion 5f, and the marker standard substances 21b, 21c, 21d, and 21e are respectively inserted into each positioning hole 5a of the remaining positioning hole-forming portions 5g, 5h, 5i, and 5j (positioning step). Incidentally, the biological tissue fragment 22 may be placed on the tray bottom 34 from the through hole 6 after the embedded block-preparing cassette 1 is placed on the tray 30, or the biological tissue fragment 22 may be placed on the tray bottom 34 after the standard substance 21 is inserted into the positioning hole 5a.

In the present embodiment, the outer shape of the standard substance 21 is columnar in accordance with the columnar shape of the positioning hole 5a, and further, the diameter of the standard substance 21 is selected to be slightly smaller than the diameter of the positioning hole 5a, and thus, the standard substance 21 can be reliably inserted into the positioning hole 5a, and the standard substance 21 can be supported in the positioning hole 5a.

Next, a liquid embedding agent, such as paraffin, that is liquefied by heating the embedding agent is poured from the opening 4 to the tray 30 (liquid embedding agent-introducing step). The liquid embedding agent is poured until the biological tissue fragment 22 on the tray bottom 34 and the standard substance positioning-portion 5 of the embedded block-preparing cassette 1 are covered. At this time, the liquid embedding agent accumulates in the space surrounded by the plate frame portion 13 of the embedded block-preparing cassette 1 on the tray bottom 34, and flows between the region of the through hole 6 and the region of the standard substance-positioning portion 5 of the block-preparing cassette 1. In addition, the liquid embedding agent accumulates in the gaps in each positioning hole 5a into which the standard substances 21 are inserted in the positioning hole-forming portions 5f, 5g, 5h, 5i and 5j or accumulates around the standard substances 21 exposed from the inside of the positioning holes 5a, and the embedding agent covers all of the biological tissue fragment 22, the standard substance-positioning portion 5 and the standard substance 21.

When the liquid embedding agent is solidified, the standard substance 21 is supported by the positioning hole, and thus, for example, the standard substance can be positioned such that the standard substance is present over the entire height range from the lower end to the upper end of the biological tissue fragment 22 with respect to the tray bottom 34. Here, when the liquid embedding agent is poured onto the tray 30 from the opening 4 of the embedded block-preparing cassette 1, the biological tissue fragment 22 on the tray bottom 34 may float above the tray bottom 34, or the position of the biological tissue fragment 22 may also be shifted. In this case, tweezers or the like can be put into the accommodating portion 31 of the tray 30 through the through hole 6 of the frame portion 3 and the biological tissue fragment 22 on the tray bottom 34 can be pressed against the tray bottom 34. Thus, the position of the biological tissue fragment 22 can be adjusted with respect to the height range of the existing standard substance 21.

Figure 4A:
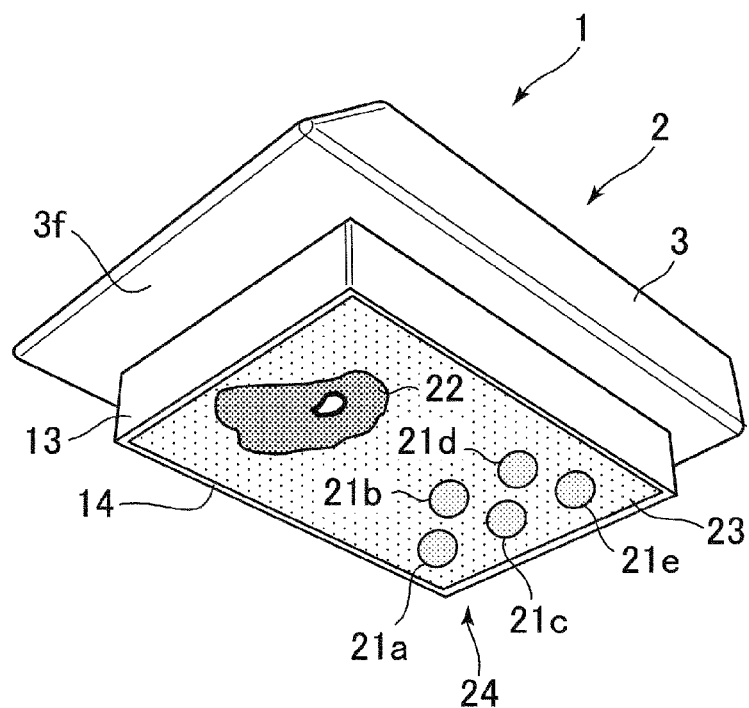
FIG. 4A is a perspective view illustrating a configuration of the embedded block before a plate frame portion is removed.
Figure 4B:
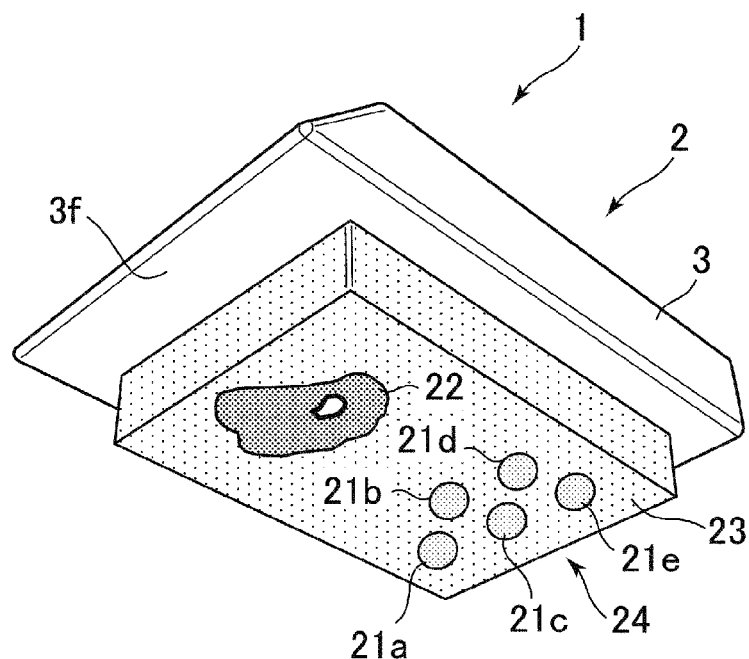
FIG. 4B is a perspective view illustrating a configuration of the embedded block after the plate frame portion is removed.

Thereafter, by cooling and solidifying the liquid embedding agent, both the biological tissue fragment 22 and the standard substance 21 are embedded in the same embedding agent 23 as illustrated in FIG. 4A in which parts that correspond to those of FIG. 3 are given the same reference numerals, and the embedded block 24 integrated with the embedded block-preparing cassette 1 can be prepared (solidifying step). Finally, as illustrated in FIG. 4B in which the parts that correspond to those of FIG. 4A are given the same reference numerals, the plate frame portion 13 provided on the lower surface 3f of the frame portion 3 is removed, and the embedded block 24 is exposed to the outside of the embedded block-preparing cassette 1. In this manner, by removing the plate frame portion 13 disposed in a quadrilateral shape in the embedded block-preparing cassette 1, a rectangular parallelepiped embedded block 24 having four corners with a shape close to a right angle can be prepared. In addition, since the liquid embedding agent is solidified including that in the standard substance-positioning portion 5 in the opening 4 of the embedded block-preparing cassette 1, the embedding agent 23 is integrated with the standard substance-positioning portion 5, and thus it is possible to prevent the embedded block 24 from falling off from the embedded block-preparing cassette 1.

(4) Tissue Section Selection Method of Present Invention

Next, an example of the tissue section selection method according to the present invention will be described. Here, similar to the "(1) Outline of Embedded Block-preparing Cassette of Present Invention", a case where the state of the biological tissue is inspected by the immunohistochemical staining method will be described as an example. First, as illustrated in FIG. 4B, an embedded block 24 in which both the biological tissue fragment 22 and the standard substance 21 are embedded in the same embedding agent 23 is prepared using the embedded block-preparing cassette 1.

Next, the embedded block-preparing cassette 1 integrated with the embedded block 24 is set on a microtome. In the microtome, for example, the position of a cutting blade is set to a desired slicing thickness (for example, 4 μm), the embedded block 24 is sliced by the microtome, and a sheet-like embedded tissue section in which the cutting surfaces of the biological tissue fragment 22 and the standard substance 21 appear on the both surfaces is prepared. With the microtome, for example, by a cutting blade that moves up and down in one stroke, the embedded tissue section is excised from the embedded block 24 per each stroke.

Figure 5:
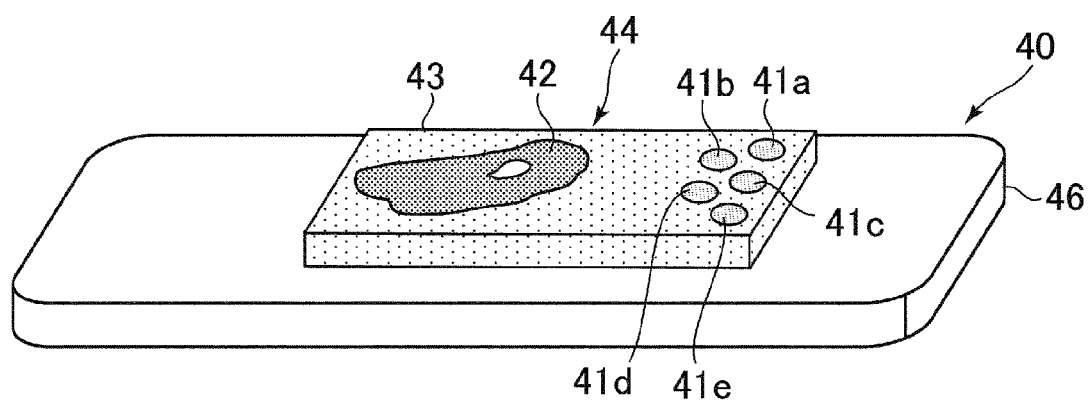
FIG. 5 is a perspective view illustrating a configuration of an embedded tissue section obtained by slicing the embedded block.

Next, as illustrated in FIG. 5, by stretching and mounting the sheet-like embedded tissue section 44 on a substrate 46, such as a slide glass, a tissue section-mounting board 40 is prepared. The embedded tissue section 44 is dried on the substrate 46. Here, the embedded tissue section 44 is formed in a rectangular shape having four corners of approximately a right angle. Therefore, by using the corners of the embedded tissue section 44 as a guide, an operator can grasp the position of the tissue section 42 in the embedded block 24 before cutting.

In the embedded tissue section 44, the tissue section 42, a thickness standard substance section 41e as a standard substance section, and marker standard substance sections 41d, 41c, 41b and 41a as the same standard substance sections are exposed to the surface, and each circumferential side of the tissue section 42, the thickness standard substance section 41e, and the marker standard substance sections 41d, 41c, 41b and 41a is configured to be surrounded by an embedding agent section 43.

Sequentially performed are, for example, an embedding agent-removing treatment for removing the embedding agent from the embedded tissue section 44, a protease treatment with an antigen retrieval solution, an endogenous peroxidase treatment with a blocking reagent, and a staining treatment with the immunohistochemical staining method. In the staining treatment, for example, after causing an antigen-antibody reaction in the tissue section 42 using a primary antibody that binds to the HER2/neu protein in the tissue section 42, a secondary antibody labeled polymer is bound to the primary antibody, and further the HER2/neu protein contained in the tissue section 42 is stained using a chromogenic reagent or the like, whereby the HER2/neu protein is specifically detected.

Next, the tissue section-mounting board 40 is placed on a stage of a microscope provided with a digital camera, the surface of the thickness standard substance section 41e is photographed by focusing on the surface of the thickness standard substance section 41e, and the image of the thickness standard substance section 41e is obtained. At this time, the image is photographed at a predetermined magnification (in the present embodiment, the objective lens magnification ratio is 2.5). In addition, the image is generated based on the reflected light from the surface of the thickness standard substance section 41e. The color tone of the image is also determined based on the reflected light.

Based on the image of the thickness standard substance section 41e, the color tone of the thickness standard substance section 41e is scored. In the present embodiment, by using a measurement program, pixels of a predetermined color tone (in the present embodiment, a color tone of a hue range of 272° to 305°, a chroma range of 0 to 51, a brightness range of a R value of 0 to 71, a brightness range of a G value of 0 to 77, and a brightness range of a B value of 0 to 77) are extracted from the image of the thickness standard substance section 41e, and the color tone is scored by using the following Equation (1). Here, since the urethane foam stained in blue is used as the thickness standard substance 21a, the above-described color tone range is selected.

$$\text{SCORE} = \sum_{\text{Chroma}} \left( \frac{255 - \text{Average Brightness}}{255} \right) \times \text{Pixel Ratio} \qquad (1)$$

Specifically, the extracted pixels are sorted by a chroma value, and the number of pixels that belong to the chroma range and an average brightness are calculated for each predetermined chroma range. The average brightness is calculated by averaging the average values of the R value, the G value and the B value of each pixel over all of the pixels that belong to each chroma range. The value obtained by subtracting the average brightness from an upper limit value 255 of the brightness value is divided by 255 to normalize the average brightness in each chroma range. A score is calculated by multiplying the average brightness normalized for each chroma range by a pixel ratio that is derived by dividing the number of pixels that belong to the chroma range by the number of extracted pixels, and then adding all the multiplication results.

Next, using a calibration curve that expresses a relationship between the score and the thickness of the thickness standard substance section 41e prepared in advance, a thickness that corresponds to the score calculated by the above-described equation is calculated, and the thickness is used as the thickness of the tissue section 42. In addition, when the thickness of the tissue section 42 is within a predetermined range (4 μm±0.4 μm in the present embodiment), the tissue section 42 on the tissue section-mounting board 40 is selected as a target to be inspected. Meanwhile, when the thickness of the tissue section 42 is not within the predetermined range, it is determined that the tissue section 42 on the tissue section-mounting board 40 is not to be inspected. In this manner, in the present embodiment, the tissue section 42 to be inspected is selected based on the color tone as a light signal from the thickness standard substance section 41e.

Subsequently, the surface of the marker standard substance section 41a is photographed while focusing on the surface of the marker standard substance section 41a to obtain an image of the marker standard substance section 41a. At this time, the image is photographed at a predetermined magnification (in the present embodiment, the objective lens magnification ratio is 40 times).

Based on the image of the marker standard substance section 41a, the staining intensity of the marker standard substance section 41a is scored based on the color tone of the marker standard substance section 41a. In the present embodiment, by using the measurement program, pixels of a predetermined color tone (a color tone of a hue of 50° to 180°, a chroma range of 2 to 40, an R value of 10 to 180, a G value of 10 to 145, and a B value of 10 to 140) are extracted from the image of the marker standard substance section 41a, the color tone is scored similarly to the thickness standard substance section 41e using the above-described Equation (1), and the score is regarded as the staining intensity score. In the present embodiment, the above-described color tone range is selected because the HER2/neu protein is stained brown.

Next, a graph is prepared, in which a vertical axis indicates the score of the staining intensity of the marker standard substance section 41a and a horizontal axis indicates a thickness of the tissue section 42, and which illustrates a calibration curve that represents a relationship between a staining intensity score of the marker standard substance section 41a and a thickness of the tissue section 42. Plotting is based on the thickness of the tissue section 42 calculated above and the staining intensity score of the marker standard substance section 41a.

As a result of plotting, when the staining intensity score of the marker standard substance section 41a is within a predetermined range (in the present embodiment, the range of the staining intensity score of the calibration curve of ±10%), staining of the HER2/neu protein in the tissue section 42 is appropriately performed, and the detection result of the marker is regarded as suitable. Accordingly, it is determined that the tissue section 42 can be inspected, and the tissue section 42 of the tissue section-mounting board 40 is selected as a target to be inspected.

Meanwhile, when the plot is not within the predetermined range, staining of the HER2/neu protein of the tissue section 42 is not appropriately performed, and there is a possibility that the detection result of the marker is not suitable, and, thus, there is a concern that an error may occur in inspection of the tissue section 42, it is determined that the tissue section 42 of the tissue section-mounting board 40 is not to be inspected. In this manner, in the present embodiment, the tissue section 42 to be inspected is selected based on the color tone as a light signal from the marker standard substance section 41a.

Accordingly, an operator who performs the inspection inspects the tissue section 42 by comparing the color tone of the selected tissue section 42 with the color tone of the marker standard substance sections 41d, 41c, 41b and 41a.

Incidentally, instead of the marker standard substance section 41a, the staining intensity score of any of the marker standard substance sections 41d, 41c and 41b may be calculated, and in a case where the staining intensity score is within a predetermined range, it may be determined that the inspection is possible. In a case where the marker standard substance section 41d consists of a negative cell line and the staining treatment is appropriately performed, the marker standard substance section cannot be stained. Thus, whether or not the staining is appropriately performed is determined based on whether or not the section 41d is stained.

Each staining intensity score is calculated with respect to two or more marker standard substances selected among the marker standard substance sections 41d, 41c, 41b, and 41a, and when the staining intensity scores of the two or more marker standard substances are within a predetermined range, it may be determined that the inspection is possible. Furthermore, each staining intensity score is calculated with respect to the marker standard substance sections 41d, 41c, 41b and 41a, and in a case where the staining intensity scores of all of the marker standard substance sections 41d, 41c, 41b and 41a are within a predetermined range, it may be determined that the inspection is possible.

(5) Action and Effect

In the above-described configuration, the embedded block-preparing cassette 1 according to the embodiment of the present invention is configured such that the box body 2 is placed on the tray 30 into which the liquid embedding agent is poured when the embedded block 24 in which the biological tissue fragment 22 is embedded in an embedding agent 23 is prepared. The box body 2 of the embedded block-preparing cassette 1 includes: the frame 3 having the through hole 6, which penetrates the upper surface 3a and the lower surface 3f in the region facing the biological tissue fragment 22 on the tray bottom 34; and the standard substance-positioning portion 5 which is provided to face the tray bottom 34 and has the positioning hole 5a into which the standard substance 21 is inserted. In addition, in the standard substance-positioning portion 5, the standard substance 21 is present within a height range from the lower end to the upper end of the biological tissue fragment 22 with respect to the tray bottom 34 when the standard substance 21 is inserted into the positioning hole 5a.

Accordingly, when the embedded block 24 is prepared in the embedded block-preparing cassette 1 while maintaining the standard substance 21 to be present within the height range from the lower end to the upper end of the biological tissue fragment 22 by means of the standard substance-positioning portion 5, the liquid embedding agent is poured into the opening 4 of the embedded block-preparing cassette 1, whereby the embedded block 24 in which the biological tissue fragment 22 and the standard substance 21 are embedded in the same embedding agent 23 can be prepared. By using the embedded block-preparing cassette 1, it is possible to prepare the embedded tissue section 44 in which the tissue section 42, the thickness standard substance section 41e, and the marker standard substance sections 41d, 41c, 41b and 41a appear on the same surface by slicing the embedded block 24. Accordingly, by using the embedded block-preparing cassette 1, the tissue section to be inspected can be selected based on the color tone of the thickness standard substance section 41e and, for example, the marker standard substance section 41a, and the inspection can be performed only on the tissue section optimum for the inspection. Thus, it is possible to suppress occurrence of an error in the inspection result.

Furthermore, in the embedded block-preparing cassette 1, the region in the opening 4 other than the region for forming the standard substance-positioning portion 5 is occupied by the through hole 6, and when seen from above, the entire biological tissue fragment 22 is accommodated in the formation region of the through hole 6. Accordingly, in the embedded block-preparing cassette 1, when the embedded block 24 is prepared, the biological tissue fragment 22 can be pressed against the tray bottom 34 through the through hole 6. Therefore, in the embedded block-preparing cassette 1, it is possible to prevent the biological tissue fragment 22 from floating up, and it is possible to adjust the position of the tissue section 42 in accordance with the height range of the thickness standard substance 21a and the marker standard substances 21b, 21c, 21d and 21e. Accordingly, by slicing the embedded block 24 prepared by using the embedded block-preparing cassette 1, it is possible to reliably prepare the embedded tissue section 44 in which all of the tissue section 42, the thickness standard substance section 41e, and the marker standard substance sections 41d, 41c, 41b and 41a appear on the same surface.

Furthermore, by using the embedded block-preparing cassette 1, the rectangular parallelepiped embedded block 24 having four corners with a shape close to a right angle can be prepared by the plate frame portion 13 of the lower surface 3f of the frame 3. Accordingly, it is possible to set the outer circumferential shape of the plurality of embedded tissue sections 44 prepared by slicing the embedded block 24 to have a quadrilateral shape having four right-angled corners. When selecting the tissue section 42 to be inspected by attaching the embedded tissue section 44 to a slide glass, it is possible to more accurately grasp the position of the tissue section 42 to be confirmed even between different slides based on the four corners of the embedded tissue section 44.

In the tissue section selection method of the present invention, the embedded block 24 is prepared by embedding all of the biological tissue fragment 22, the thickness standard substance 21a, and the marker standard substances 21b, 21c, 21d and 21e in the same embedding agent 23 (embedded block-preparing step), and the sheet-like embedded tissue section 44 in which all of the tissue section 42, the thickness standard substance section 41e, and the marker standard substance sections 41d, 41c, 41b and 41a appear on the same surface is prepared by slicing the embedded block 24 (embedded tissue section preparing step). In addition, according to the tissue section selection method, the tissue section to be inspected is selected by calculating the thickness of the tissue section 42 based on the color tone (light signal) of the thickness standard substance section 41e (tissue section selecting step, tissue section thickness determining step), and the tissue section 42 to be inspected is selected based on, for example, the color tone (light signal) of the marker standard substance section 41a after the tissue section thickness determining step (tissue section selecting step, marker suitability determining step).

Accordingly, the tissue section selection method enables calculation of the thickness of the tissue section 42 from the color tone of the thickness standard substance section 41e by using the sheet-like embedded tissue section 44 in which the tissue section 42 and the thickness standard substance section 41e appear on the same surface. Thus, according to the tissue section selection method, only the tissue section 42 having an optimum thickness for the inspection is selected, and the inspection can be performed only on the selected tissue section 42, whereby, it is possible to suppress an error in the inspection result.

According to the tissue section selection method, it is possible to calculate a staining intensity score from the color tone of the marker standard substance section 41a by using the embedded tissue section 44 in which the tissue section 42 and the marker standard substance section 41a appear on the same surface. In this case, according to the tissue section selection method, the tissue section 42 to be inspected is selected based on the staining intensity score of the marker standard substance section 41a. Therefore, according to the tissue section selection method, it is possible to more accurately determine the suitability of the detection result of the marker, and thus the inspection can be performed only on the tissue section 42 optimum for the inspection, thereby enabling suppression of an error in the inspection result.

Particularly, in the tissue section selection method, after selecting the tissue section 42 to be inspected by calculating the thickness of the tissue section 42 based on the color tone of the thickness standard substance section 41e, a staining intensity score is further calculated based on the color tone of the marker standard substance section 41a, and then the tissue section 42 to be inspected is selected. Thus, according to the tissue section selection method, it is possible to select only the tissue section 42 having a desired thickness and determine suitability of the detection result of the marker with respect to the selected tissue section 42. Thus, it is possible to suppress occurrence of an error in the inspection result.

In the tissue section selection method, it is possible to prepare the embedded tissue section 44 in which the tissue section 42 and the marker standard substance sections 41d, 41c, 41b and 41a appear on the same surface by slicing the embedded block 24. Thus, it is possible to compare during inspection the stained tissue section 42 with the marker standard substance sections 41d, 41c, 41b and 41a all of which were prepared and stained under the same condition. Therefore, it is possible to prevent the influence due to the difference in preparation conditions and/or the staining conditions, and to more accurately perform the inspection with respect to the tissue section 42.

(6) Modified Example

Incidentally, the present invention is not limited to the above-described embodiment, and various modifications can be made within the scope of the gist of the present invention. For example, the shape, size and the like of the tray 30 are not particularly limited, and can be appropriately selected in accordance with the embedded block-preparing cassette 1. For example, those which are conventionally sold under the name of an embedding dish or the like can be used as the tray 30, or the tray may be prepared in accordance with the shape, size and the like of the embedded block-preparing cassette. Further, the number of positioning holes 5a may be the same as the number of standard substances 21, or may be equal to or greater than the number of standard substances 21.

Figure 6:
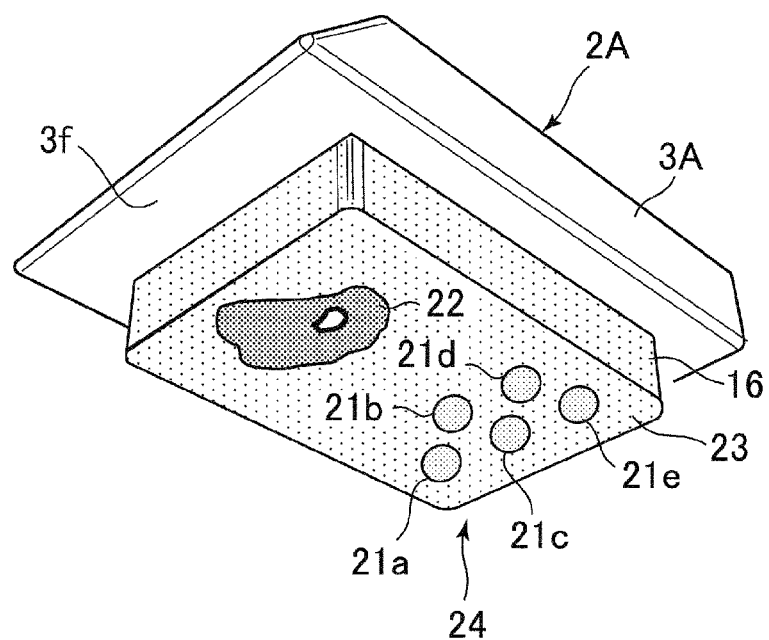
FIG. 6 is a perspective view illustrating a configuration of an embedded block prepared using an embedded block-preparing cassette of a modification example.

In the above-described embodiment, while a case where the plate frame portion 13 is provided on the lower surface 3f of the frame 3 has been described, the present invention is not limited thereto, and the plate frame portion 13 may not be provided on the lower surface 3f of the frame 3. FIG. 6 in which the parts that correspond to those of FIG. 4B are given the same reference numerals is a schematic view illustrating a configuration when the embedded block 24 is prepared by using the embedded block-preparing cassette 1 in which the plate frame portion 13 is not provided on the lower surface 3f of the frame 3. As illustrated in FIG. 6, the embedding agent 23 in the embedded block 24 can have the same outer shape as that of the accommodating portion 31 of the tray 30. Therefore, for example, although the plate frame portion 13 is not provided, the embedding agent 23 has the four rounded corners in the rectangular parallelepiped shape. However, the operation of removing the plate frame portion 13 as illustrated in FIGS. 4A and 4B becomes unnecessary, and thus it is possible to reduce the work burden.

In the above-described embodiment, while the thickness standard substance 21a and the marker standard substances 21b, 21c, 21d and 21e are used, and thus the standard substance-positioning portion 5 provided with the five positioning holes 5a has been described, the present invention is not limited thereto, and any standard substance-positioning portion provided with at least one positioning hole, such as one positioning hole or two positioning holes, may be used. In particular, it is desirable to have at least two positioning holes such that each of the thickness standard substance 21a and the marker standard substance 21e can be embedded one-by-one in the embedded block 24.

Figure 7A:
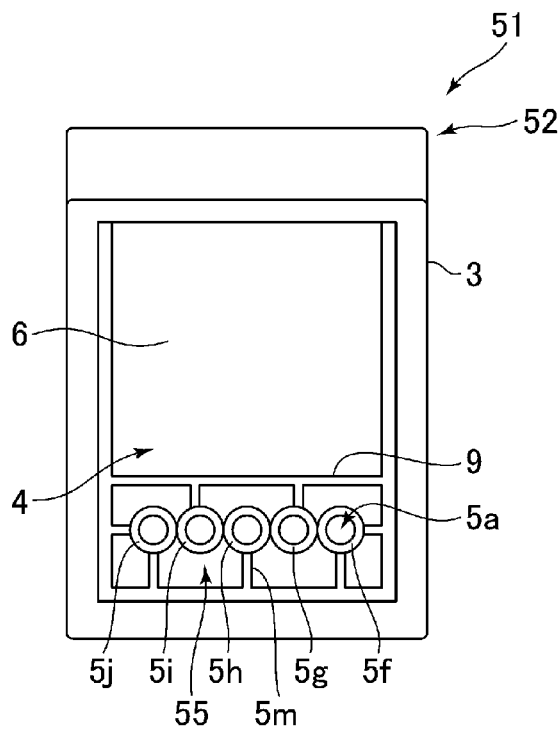
FIG. 7A is a top view of the embedded block-preparing cassette having a standard substance-positioning portion in which five positioning holes are disposed in a row.
Figure 7B:
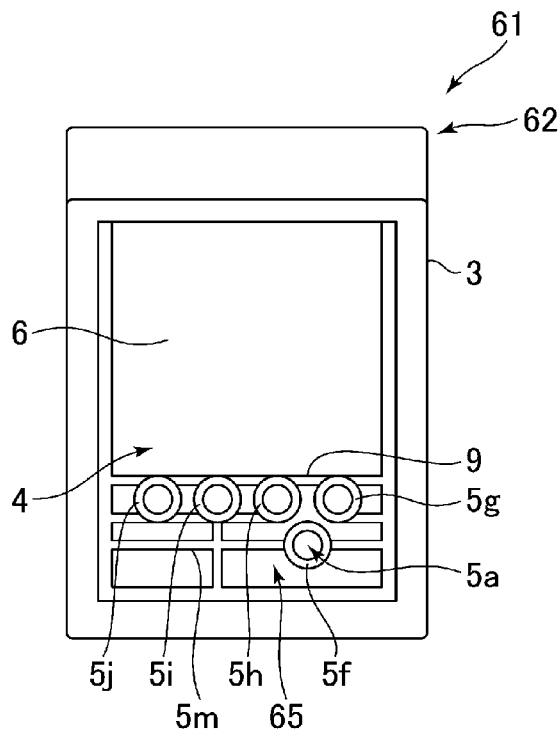
FIG. 7B is a top view of the embedded block-preparing cassette having a standard substance-positioning portion in which four positioning holes are disposed in a row.

In the above-described embodiment, the standard substance-positioning portion 5 in which the three positioning hole-forming portions 5f, 5h and 5j arranged in series and the two positioning hole-forming portions 5g and 5i arranged in series are arranged in two rows. But the present invention is not limited thereto, and the positioning hole-forming portions may be disposed in various positions such as in one row or three rows in the standard substance positioning portion. For example, FIGS. 7A and 7B are schematic views illustrating an upper surface configuration of the embedded block-preparing cassettes 51 and 61 according to another embodiment. As illustrated in FIG. 7A, the opening 4 in a box body 52 may be provided with a standard substance positioning portion 55 in which a plurality of positioning hole-forming portions 5f, 5g, 5h, 5i and 5j are arranged in one row. Further, as illustrated in FIG. 7B, four positioning hole-forming portions 5g, 5h, 5i and 5j may be arranged in one row in the opening 4 of a box body 62, and also may be provided a standard substance-positioning portion 65 in which the remaining one positioning hole-forming portion 5f is disposed in a position different from the row of the positioning hole-forming portions 5g, 5h, 5i and 5j.

The height of the standard substance 21 has desirably such length that the standard substance 21 can be supported by the positioning hole-forming portion in a state where one end of the standard substance 21 abuts the tray bottom 34 although the present invention is not limited thereto. For example, in the above-described embodiment, the standard substance 21 is disposed over the entire height range of the biological tissue fragment 22 using the standard substance 21 that is equal to or higher than the height range of the biological tissue fragment 22, but the present invention is not limited thereto. For example, a standard substance may be disposed only in a part of the region of the height range of the biological tissue fragment 22 using a standard substance shorter than the height range of the biological tissue fragment 22.

In the above-described embodiment, a case where the hole shape of each positioning hole 5a in the standard substance-positioning portion 5 is columnar and the standard substance 21 has a columnar shape in conformity with the columnar hole shape has been described. However, the present invention is not limited thereto, and the hole shape of each positioning hole 5a in the standard substance-positioning portion 5 may be formed to be various other types, such as a quadrangular columnar shape or a polygonal columnar shape, and in conformity therewith, the standard substance 21 may also be formed to various other shapes, such as a quadrangular columnar shape or a polygonal columnar shape. Further, as long as the standard substance 21 can be supported by being inserted into the positioning hole 5a, the shape of the positioning hole-forming portion, the shape of the positioning hole, and the shape of the standard substance are not particularly limited, and for example, the shape of the positioning hole and that of the standard substance may be different.

In the above-described embodiment, while a case where both the standard substance-positioning portion 5 and the through hole 6 are provided in the region in the opening 4 has been described, the present invention is not limited thereto. For example, different from the opening 4 in which the through hole 6 is formed, an opening which penetrates the upper surface and the lower surface may be provided in the frame 3, and the standard substance-positioning portion 5 may be provided in the opening.

Figure 8A:
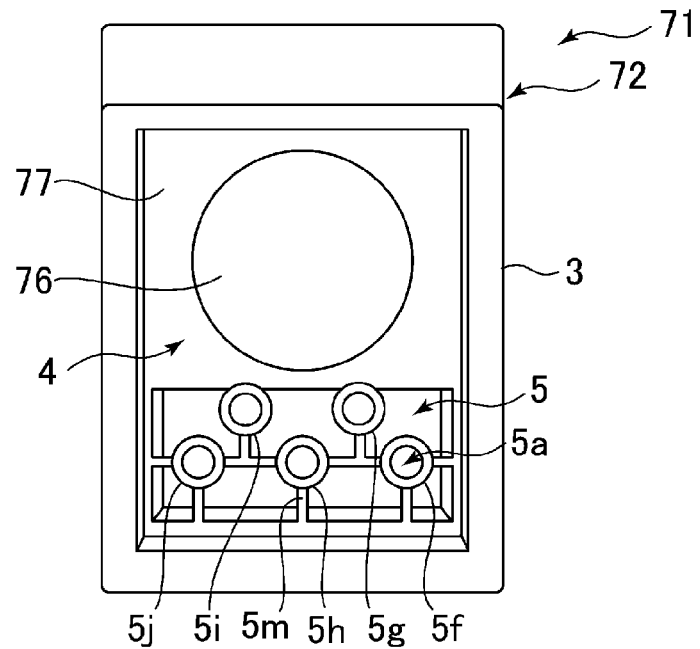
FIG. 8A is a top view of the embedded block-preparing cassette in which a through hole has a circular shape.
Figure 8B:
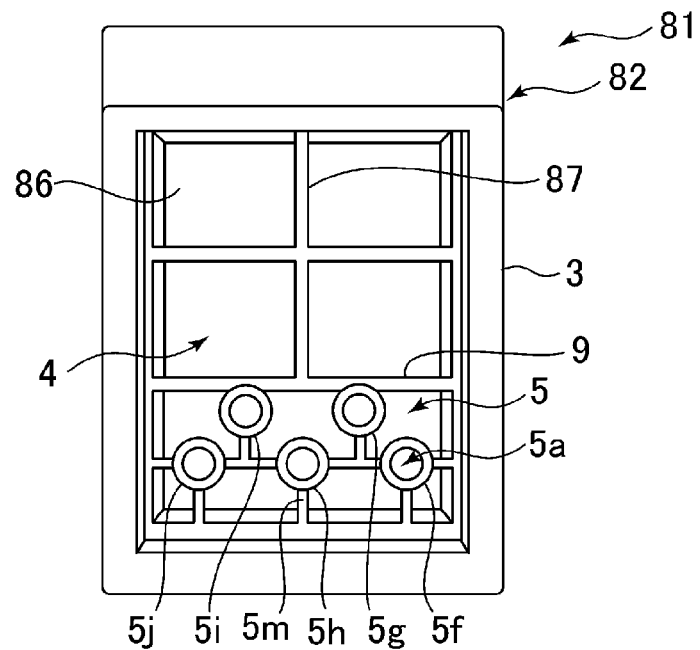
FIG. 8B is a top view of an embedded block-preparing cassette in which a through hole is divided into four.

In the above-described embodiment, while a case where the quadrilateral through hole 6 is provided in one of the regions in the opening 4 divided into two by the horizontal bar 9 has been described, the present invention is not limited thereto, and, for example, a through hole having a circular, triangular, elliptical or polygonal shape, or the like may be provided. For example, FIG. 8A is a schematic view illustrating the upper surface configuration of an embedded block-preparing cassette 71 according to another embodiment. As illustrated in FIG. 8A, a plate-like through hole-forming portion 77 having a circular through hole 76 may be provided in the opening 4 of a box body 72. In addition, in the above-described embodiment, although a case where one through hole 6 is provided has been described, the present invention is not limited thereto. For example, FIG. 8B is a schematic view illustrating the upper surface configuration of an embedded block-preparing cassette 81 according to another embodiment. As illustrated in FIG. 8B, in a partial region of the opening 4 of a box body 82, may be provided a cross-shaped horizontal bar 87 having a cross shape in which two prismatic members are orthogonal to each other, and a through hole 86 divided into four.

In the above-described embodiment, while a case where the positioning hole-forming portions 5f, 5g, 5h, 5i, and 5j are fixed to the inner wall 3b of the frame 3 by the horizontal bar 9 provided on the inner wall 3b of the frame 3 or the connecting portion 5m has been described, the present invention is not limited thereto, and the positioning hole-forming portions 5f, 5g, 5h, 5i and 5j may be fixed to the inner wall 3b of the frame 3 only by the horizontal bar 9 or only by the connecting portion 5m. The positioning hole-forming portions 5f, 5g, 5h, 5i and 5j may be directly fixed to the inner wall 3b of the frame 3 without using the horizontal bar 9 or the connecting portion 5m.

In the above-described embodiment, the tissue section 42 to be inspected is selected based on the color tone of the thickness standard substance section 41e after performing the staining treatment by the immunohistochemical staining method. However, the present invention is not limited thereto, and after selecting the tissue section 42 to be inspected based on the color tone of the thickness standard substance section 41e, a treatment by the immunohistochemical staining method may be performed only on the tissue section-mounting board 40 having the selected tissue section 42.

In the above-described embodiment, the corner of the embedded tissue section 44 is used in order to more accurately grasp the observation position of the tissue section 42 between each slide. However, in order to manage the observation position with higher accuracy, may be used, for example, a microscope system having a position synchronization function of a slide glass having a reference for position management, a high accuracy XY stage having means for correcting a rotation error of the placed slide glass when the slide glass is placed, or the like.

In the above-described embodiment, the color tone of the thickness standard substance section 41e and the staining intensity of the marker standard substance section 41a are scored using the image taken by the digital camera and the above-described Equation (1). However, the present invention is not limited thereto, and the color tone of the thickness standard substance section 41e and the color tone of the marker standard substance section 41a may be visually observed using a microscope, and the score may be determined based on a color sample, a tissue section determination example or the like.

The above-described embodiment has been described by way of an example wherein the tissue section is selected to be used for the inspection method for specifically detecting the HER2/neu protein contained in the biological tissue by the immunohistochemical staining method and inspecting the state of the living body. However, the present invention is not limited thereto, and the present invention may be applied as a marker to a case of detecting ALK fusion protein, PD-L1, estrogen receptor, progesterone receptor, EGF receptor, somatostatin, S-100, and the like by an immune tissue staining method.

Furthermore, the present invention may be applied to a case of selecting a tissue section used for an inspection method for inspecting the state of a living body by specifically detecting specific genes (markers), such as HER2/neu, ALK, PD-L1, estrogen receptor and progesterone receptor contained in the tissue section by a fluorescence in situ hybridization (FISH) method or a chromogenic in situ hybridization (CISH) method.

In the FISH method, a marker in the tissue section is detected by binding the marker in the tissue section to a probe to which a fluorescent label is bound by hybridization, and then detecting fluorescence of the tissue section with a fluorescence microscope. In this case, a fluorescence intensity as a light signal from the standard substance section is scored, and the tissue section 42 to be inspected is selected based on the thickness of the tissue section 42 and the fluorescence intensity score.

In the CISH method, a marker in the tissue section is detected by binding the marker in the tissue section to a probe to which an alkaline phosphatase-labeled anti-digoxigenin (DIG) antibody or the like is bound by hybridization, and by detecting chromogenic development of the alkaline phosphatase substrate. In this case, a chromogenic intensity as a light signal from the standard substance section is scored, and the tissue section 42 to be inspected is selected based on the thickness of the tissue section 42 and the chromogenic intensity score.

In the case of the FISH method or the CISH method described above, the marker standard substance including the markers used for each method is prepared, and the marker standard substance may be inserted into the positioning hole 5a in the embedded block-preparing cassette 1 during preparation of the embedded block.

In the above-described embodiment, a case where a pigment-containing urethane foam is used as the thickness standard substance 21a has been described. However, the present invention is not limited thereto, and various cells that express an endogenous protein can also be used as the thickness standard substance 21a. In this case, the endogenous protein exhibiting a constant expression level in various cells is stained by the immunohistochemical staining, and the color tone of the staining intensity of the cells is detected as a light signal. As the cells, for example, cells that express endogenous proteins, such as β-actin, COX-4, GAPDH, lamin B1, PCNA, tubulin and CD34, can be used. More specifically, for example, HER2 positive cell line SK-BR-3, cell line MDA-MB-453, or Hela cells derived from human cervical cancer and the like can be used. Since the expression level of the endogenous protein is substantially constant in each cell, the amount of cells changes corresponding to the thickness of the thickness standard substance 21a, and the expression level of the endogenous protein also changes. In addition, the color tone of the staining intensity by the immunohistochemical staining changes corresponding to the thickness of the cells. Therefore, by using the cell as the thickness standard substance 21a, the thickness of the tissue section 42 can be calculated based on the color tone of the thickness standard substance 21a, and the tissue section 42 used for the inspection can be selected.

In a case where the cell that expresses a marker such as, for example, HER2/neu protein in addition to the endogenous protein is used as the thickness standard substance 21a, the thickness standard substance 21a can also be used as a marker standard substance. In this case, first, the embedded tissue section 44 is prepared using the thickness standard substance 21a, and the endogenous protein and the marker which are expressed in the thickness standard substance section 41e are respectively stained by the immunohistochemical staining. Next, the surface of the thickness standard substance section 41e is photographed. Subsequently, the staining intensity score of the endogenous protein and the staining intensity score of the marker are respectively calculated using the above-described Equation (1) from the image of the thickness standard substance section 41e, and the ratio between the score of the endogenous protein and that of the marker is calculated. When the ratio of the scores is within a predetermined value range, it is determined that the staining treatment is appropriate, and the tissue section 42 is selected as a tissue section to be inspected. Since the endogenous protein and the marker are stained in different colors, the score of the endogenous protein and the score of the marker can be calculated from the image of one fragment of the thickness standard substance section 41e.

(7) Verification Experiment (7-1) Verification Experiment 1

In verification experiment 1, a blue pigment-containing urethane foam is used as the thickness standard substance, and a relationship between the color tone of the blue pigment-containing urethane foam and the thickness of the tissue section was verified. Incidentally, as illustrated in FIG. 5, the embedded tissue section 44 has the embedding agent section 43 and the tissue section 42 formed on the same surface, and thus the thickness of the embedding agent section 43 was deemed as the thickness of the tissue section 42. In addition, since it is considered that the embedded tissue section has no significant change in the gradient of the calibration curve to be prepared regardless whether or not the embedded tissue section includes a tissue section, a section in which the tissue section 42 is not embedded was used hereinafter as the embedded tissue section for verification.

(7-1-1) Preparation of Thickness Standard Substance

To a polyol which is a soft urethane foam material, a foaming agent, a foam stabilizer and a catalyst, a blue pigment (manufactured by Resino Color Industries) in an amount of 4.5% of the total mass was added and mixed by stirring. By foaming the mixed material after molding, a blue pigment-containing urethane foam having a size of 100 to 110 mm in length, 60 to 70 mm in width and 30 to 40 mm in height, and a weight of 35 to 45 g was prepared.

The blue pigment-containing urethane foam was cut in a height direction into a sheet with a width of approximately 5 mm such that a cutting surface is parallel to the lateral direction of the blue pigment-containing urethane foam. Subsequently, from the sheet-like blue pigment-containing urethane foam, a part of the vicinity of the center where the number of bubbles contained in the blue pigment-containing urethane foam is small was excised, and sheet-like small urethane foam fragments having a thickness of approximately 5 mm were prepared.

The small urethane foam fragments were placed in a commercially available paraffin-embedded block-preparing cassette EB-W (manufactured by Olympus), and an immobilization treatment is performed using a closed type automatic immobilization embedding apparatus Tissue-Tek VIP (manufactured by Sakura Finetek Japan). A thickness standard substance was prepared by hollowing out the immobilized small urethane foam fragment into a columnar shape by using tissue micro-arrayer apparatus KIN-2-type (manufactured by Azumaya Medical Instruments Co., Ltd.).

(7-1-2) Preparation of Embedded Block Containing Thickness Standard Substance

In order to prepare an embedded tissue section for verification in which the tissue section 42 is not embedded, the embedded block-preparing cassette 1 was placed on the tray 30 without placing a biological tissue section on the tray bottom 34. The thickness standard substance 21a was inserted into the positioning hole 5a in the embedded block-preparing cassette 1, and then liquefied paraffin was poured from the opening 4 of the embedded block-preparing cassette 1. After the paraffin was cooled and solidified, the embedded block-preparing cassette 1 was removed from the tray 30, and the plate frame portion 13 was removed to obtain an embedded block in which only the thickness standard substance 21a was embedded.

(7-1-3) Preparation of Embedded Tissue Section for Verification

The embedded block in which only the thickness standard substance 21a was embedded was set in the microtome (manufactured by Daiwa Koki Kogyo Co., Ltd.). The slicing thickness of the microtome was set to 2 µm, the embedded block was sliced by the microtome, and ten embedded tissue sections for verification having a nominal thickness (hereinafter, referred to as nominal thickness) of 2 µm were prepared. The thickness standard substance sections 41e were exposed on both surfaces of the embedded tissue sections for verification.

Similarly, ten embedded tissue sections for verification each of which has a nominal thickness of 3 µm, 4 µm, 5 µm, and 6 µm were prepared. The embedded tissue sections for verification were attached to a slide glass (manufactured by Muto Glass Industrial Co., Ltd., Japan) one by one, and then dried at 37° C. overnight. In addition, the embedded tissue sections for verification have the same configuration as the embedded tissue section illustrated in FIG. 5 except that they do not include the tissue section and the marker standard substance section, and the circumference of the thickness standard substance section 41e is surrounded by a sheet-like embedding agent section.

(7-1-4) Preparation of Calibration Curve for Calculating Thickness of Tissue Section A slide glass with the embedded tissue section for verification was placed on a sample stage of the microscope system (manufactured by Nikon Co., Ltd.) maintained horizontally, and the height of the embedding agent section from the board was measured at four locations using optical interferometry by means of Vert Scan (registered trademark, manufactured by Ryoka System Co., Ltd., Ver. 1.0.3). The average value of the height measured at four locations was regarded as the thickness of the tissue section. The measurement conditions of Vert Scan were set as follows: the wavelength filter: 530White, the two-beam interference objective lens magnification: 10 times, the measurement mode: Wave mode.

A method for measuring the thickness of the embedding agent section will be specifically described. The XY stage, Z stage, and tilt stage of the sample stage of the microscope system were adjusted such that one of the four sides of the embedding agent section was projected on a measurement screen of a monitor attached to the microscope system, and the sample stage of the microscope was moved. A vertically moving handle was operated and adjusted to obtain the strongest contrast in the interference fringes in the image displayed on the monitor. The gradient of the sample stage was adjusted so that the number of the interference fringes in the image of the monitor becomes approximately 2 to 7. Measurement was performed, and whether or not the slide glass was placed horizontally was further confirmed by using as an indication that the color tone of the slide glass region in the measurement screen of the monitor is constant.

Subsequently, a partial region of the slide glass surface used as a reference for the thickness of the embedding agent section was designated, and a correction treatment for removing the influence of surface roughness and waviness of the designated region was performed. A partial region of the surface of the embedding agent section was designated, and the height of one side of the embedding agent section was measured with respect to the designated region of the slide glass surface after the correction treatment. The operation was also performed on the other three sides of the embedding agent section, and the average value of the measured heights of the four sides was regarded as the thickness of the tissue section.

Similarly, the thickness of the tissue section was calculated for all of the prepared embedded tissue sections for verification. Excluded were those embedded tissue sections for verification in which a difference in thickness of any one of the four sides of the embedding agent section from the nominal thickness exceeds 2.0 µm, and those embedded tissue sections for verification in which the thickness of the tissue section is calculated to have an existence probability of less than 0.3% when the variation in thickness is regarded as a normal distribution. As a result, a total of forty-two embedded tissue sections for verification were obtained, which include seven embedded tissue sections for verification having a nominal thickness of 2 µm, seven embedded tissue sections for verification having a nominal thickness of 3 µm, nine embedded tissue sections for verification having a nominal thickness of 4 µm, ten embedded tissue sections for verification having a nominal thickness of 5 µm, and nine embedded tissue sections for verification having a nominal thickness of 6 µm.

With respect to the forty-two embedded tissue sections for verification, by performing a deparaffinization treatment by a general method that has been already established, only the thickness standard substance section 41e was allowed to be present on the slide glass by removing the embedding agent section. In order to prevent the thickness standard substance section 41e from drying over time, a mounting medium was dropped onto the slide glass to cover the thickness standard substance section 41e with a cover glass.

Next, a slide glass on which the thickness standard substance section 41e was mounted was placed on the stage of the microscope (manufactured by Carl Zeiss Co., Ltd.) provided with a digital camera (manufactured by Canon Inc., EOS-1D), and the surface of the thickness standard substance section 41e was photographed by focusing on the surface of the thickness standard substance section 41e. Thus, an image of the thickness standard substance section 41e was obtained (photographing conditions: objective lens magnification: 2.5 times, shutter speed: 1/250, ISO: 800, LED: 19.9%, WB correction: A9/G9).

Based on the image of the thickness standard substance section 41e, the color tone of the thickness standard substance section 41e was scored using a measurement program (manufactured by Canon Inc.). Specifically, by using the measurement program, the pixels of the color tone in a hue range of 272° to 305°, a chroma range of 0 to 51, a brightness range of a R value of 0 to 71, a brightness range of a G value of 0 to 77, and a brightness range of a B value of 0 to 77 were extracted from the image of the thickness standard substance section 41e, and the color tone was scored by using the above-described Equation (1).

Figure 9:
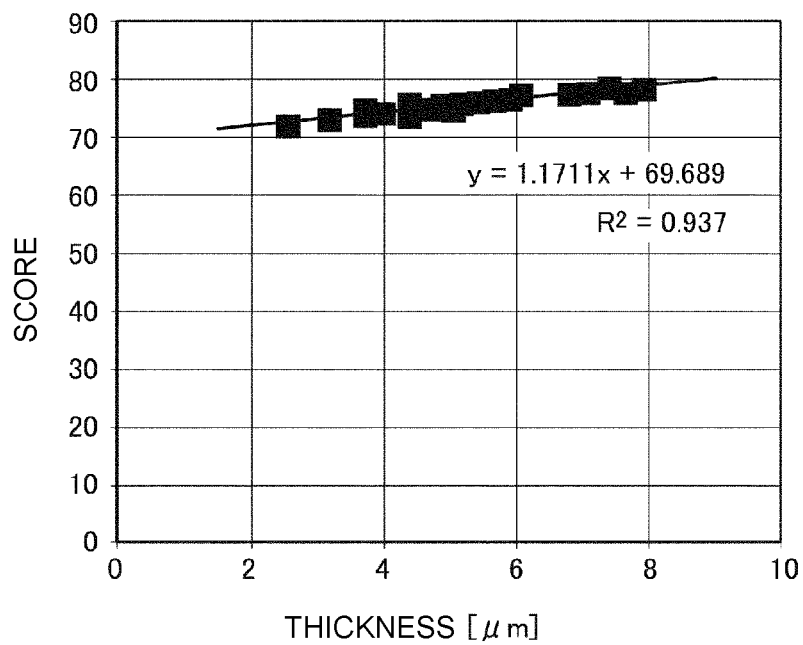
FIG. 9 is a graph illustrating a calibration curve that shows a relationship between a thickness of a tissue section and a color tone of a thickness standard substance.

In addition, as illustrated in FIG. 9, the result was plotted, wherein a horizontal axis indicates a thickness of the tissue section (height average value of the embedding agent section), and a vertical axis indicates a score of the color tone of the thickness standard substance section 41e. A linear approximate equation was calculated by the least square method based on the plot, and was regarded as a calibration curve. By the linear approximate equation calculated by the least square method, it was possible to prepare a calibration curve having a high correlation coefficient.

In this manner, since the thickness of the tissue section and the score of the color tone of the thickness standard substance section 41e are in a proportional relationship, it is possible to calculate from the color tone of the thickness standard substance section 41e, by using the calibration curve, the thickness of the tissue section that is embedded in the same embedded tissue section as the thickness standard substance section 41e.

In addition, for example, with respect to the embedded tissue section prepared by setting the slicing thickness by the microtome to 4 µm, it is possible to calculate the thickness of the tissue section from the color tone of the blue pigment-containing urethane foam (thickness standard substance section 41e) on the slide glass after attaching the embedded tissue section to the slide glass and effecting a deparaffinization treatment and a staining treatment. The tissue section in which the thickness is within a predetermined thickness range centering on 4 µm can be selected as a tissue section to be inspected. In this manner, it was possible to confirm that the calibration curve that represents a relationship between the thickness of the tissue section and the color tone of the thickness standard substance could be an index for selecting the tissue section to be inspected.

(7-2) Verification Experiment 2

In verification experiment 2, by using cells that express β-actin as the thickness standard substance 21a, the relationship between the color tone of the cells and the thickness of the tissue section 42 was verified. In addition, since the embedded tissue section 44 has the embedding agent section 43 and the tissue section 42 formed on the same surface, as illustrated in FIG. 5, the thickness of the embedding agent section 43 was regarded as the thickness of the tissue section 42. Further, since it is considered that the embedded tissue section 44 has no significant change in the gradient of the calibration curve to be prepared between the cases where an embedded tissue section 44 includes the tissue section 42 and does not include the tissue section 42, an embedded tissue section in which the tissue section 42 is not embedded was used hereinafter as the embedded tissue section for verification.

(7-2-1) Preparation of Anti-β-Actin Rabbit Polyclonal Antibody

Antiserum was collected from a rabbit immunized with β-actin synthetic peptide, and anti-β-actin rabbit polyclonal antibody was prepared by antibody purification. A marker of a control sample was stained by immunohistochemical staining by using this antibody as a primary antibody and the staining results were evaluated. it was confirmed that it was possible to stain the marker with a smaller amount of this antibody compared with the case where an existing anti-β-actin monoclonal antibody (c4 SC-47778, manufactured by Santa Cruz Biotechnology, Inc.) was used. In the verification experiment 2, the anti-β-actin rabbit polyclonal antibody prepared as described above was used.

(7-2-2) Preparation of Thickness Standard Substance

In the verification experiment 2, an HER2 positive cell line SK-BR-3 (corresponding to HER2 IHC score 3+) was used as a cell. First, a paraffin-embedded block in which only the SK-BR-3 cell line was embedded in paraffin was prepared, and the paraffin-embedded block was hollowed out using a tissue arrayer apparatus type KIN-2 (manufactured by Azumaya Medical Instruments Co., Ltd.) to give a thickness standard substance 21a.

(7-2-3) Preparation of Embedded Block Containing Thickness Standard Substance

In order to prepare an embedded tissue section for verification in which the tissue section 42 is not embedded, here, the embedded block-preparing cassette 1 was placed on the tray 30 without placing the biological tissue fragment 22 on the tray bottom 34. The thickness standard substance 21a was inserted into the positioning hole 5a in the embedded block-preparing cassette 1, and then liquefied paraffin was poured from the opening 4 of the embedded block-preparing cassette 1. After the paraffin was cooled and solidified, the embedded block-preparing cassette 1 was removed from the tray 30, and the plate frame portion 13 was removed to obtain an embedded block in which only the thickness standard substance 21a was embedded.

(7-2-4) Preparation of Embedded Tissue Section for Verification

An embedded block in which only the thickness standard substance 21a was embedded was set in the microtome (manufactured by Daiwa Koki Kogyo Co., Ltd.). The slicing thickness of the microtome was set to 2 µm, and the embedded block was sliced by the microtome to give ten embedded tissue sections for verification having a nominal thickness (hereinafter, referred to as nominal thickness) of 2 µm. The thickness standard substance sections 41e were exposed on both surfaces of the embedded tissue sections for verification.

Similarly, ten embedded tissue sections for verification were prepared for each nominal thickness of 3 µm, 4 µm, 5 µm, and 6 µm, and fifty (50) in total of embedded tissue sections for verification were prepared. The embedded tissue sections for verification were attached to the slide glass (manufactured by Muto Glass Industrial Co., Ltd.) one by one, and then dried at 37° C. overnight. Incidentally, the embedded tissue section for verification has the same configuration as the embedded tissue section 44 illustrated in FIG. 5 except that the tissue section and the marker standard substance section are not included, and the circumference of the thickness standard substance section 41e is surrounded by the sheet-like embedding agent section 43.

(7-2-5) Preparation of Calibration Curve for Calculating Thickness of Tissue Section In the same manner as that in the verification experiment 1, the height of the embedding agent section of the embedded tissue section for verification was measured, and the thickness of the embedding agent section was calculated. After calculating the thickness of the embedding agent section for each embedded tissue section for verification, the deparaffinization treatment and antigen retrieval treatment (100° C., 40 minutes, pH 6) were performed according to a general method already established on the embedded tissue section for verification attached to the slide glass. After removing the endogenous peroxidase, the thickness standard substance section 41e was washed with PBS, and a primary antibody reaction with the anti-actin rabbit polyclonal antibody prepared in the "(7-2-1) Preparation of Anti-β-Actin Rabbit Polyclonal Antibody" was performed on β-actin expressed in HER2 positive cells in the thickness standard substance section 41e. The thickness standard substance section 41e was washed again, and Simple Stain MAX-PO (MULTI) (manufactured by Nichirei Biosciences Inc.) was dropped onto the thickness standard substance section 41e at a concentration of 4 µg/ml, and secondary antibody reaction was performed at room temperature for 30 minutes. The thickness standard substance section 41e washed again was subjected to DAB staining by a general method and washed again, and nuclear staining was performed using Mayer's Hematoxylin solution. After the thickness standard substance section 41e was washed and subjected to dehydration, permiation, and medium-mounting, it was covered with a cover glass.

The thickness standard substance section 41e on which the above-described β-actin staining treatment was performed was placed on the slide glass and the slide glass was placed on the sample stage of the microscope (manufactured by Carl Zeiss), and by focusing on the cell membrane of the cell in which the stain of DAB was confirmed by the objective lens at a magnification ratio of 40, the thickness standard substance section 41e was photographed by the camera (manufactured by Canon Inc., EOS-1D) mounted on the microscope (shutter speed: 1/250, ISO: 800, LED: 19.9%, WB correction: A9/G9). From the photographed image, pixels having a specific color tone (hue: 272-305°, chroma range: 0 to 51, R: 0 to 71, G: 0 to 77, B: 0 to 77) were extracted by using the measurement program (manufactured by Canon Inc.), and the color tone of the staining intensity of the thickness standard substance section 41e was scored using the above-described Equation (1).

Figure 10:
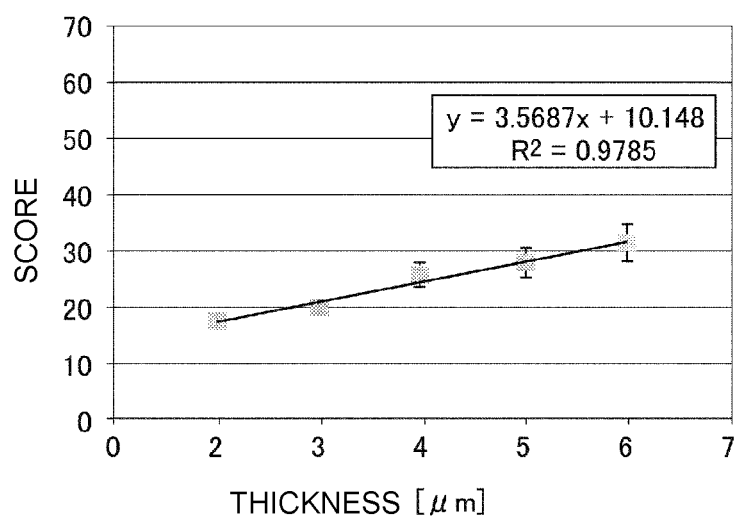
FIG. 10 is a graph illustrating a calibration curve that represents a relationship between a thickness of a tissue section and a color tone of a thickness standard substance.

Then, as illustrated in FIG. 10, the result was plotted, wherein a horizontal axis indicates the thickness of the tissue section (height average value of the embedding agent section), and a vertical axis indicates the score of the color tone of the thickness standard substance section 41e, and a linear approximate equation was calculated by the least squares method based on the plot, and this was regarded as the calibration curve. In the linear approximate equation calculated by the least squares method, it was possible to prepare a calibration curve having a high correlation coefficient.

Accordingly, since the thickness of the tissue section and the score of the color tone of the staining intensity of the thickness standard substance section 41e were in a proportional relationship, it is possible to calculate the thickness of the tissue section embedded in the same embedded tissue section as the thickness standard substance section 41e by using the calibration curve from the color tone of the thickness standard substance section 41e.

In addition, for example, with respect to the embedded tissue section prepared by setting the slicing thickness by the microtome to 4 µm, it is possible, by attaching the embedded tissue section to the slide glass, to calculate the thickness of the tissue section from the color tone of the stained cell (thickness standard substance section 41e) which express β-actin on the slide glass after a deparaffinization treatment and a staining treatment. The tissue section in which the thickness is within a predetermined thickness range centering on 4 µm can be selected as a tissue section to be inspected. Thus, even in a case where the cell which expresses endogenous protein was used as the thickness standard substance, it was confirmed that the calibration curve that represents a relationship between the thickness of the tissue section and the color tone of the thickness standard substance could be an index for selecting the tissue section to be inspected.

(7-3) Verification Experiment 3

In verification experiment 3, a relationship between the staining intensity score based on the color tone of the stained marker standard substance and the thickness of the tissue section was verified. The thickness of the tissue section is calculated using the same method as that in the verification experiment 1. In addition, following the verification experiment 1, an embedded tissue section for verification that did not contain a tissue section and a thickness standard substance was used as the embedded tissue section.

(7-3-1) Preparation of Marker Standard Substance

In the verification experiment 3, similar to the above-described embodiment, a marker standard substance 21b made from the cell line MDA-MB-231 that exhibits negative staining result, a marker standard substance 21c made from the cell line MDA-MB-175VII that exhibits a staining result of 1+, a marker standard substance 21d made from the cell line MDA-MB-453 that exhibits a staining result of 2+, and a marker standard substance 21e made from the cell line SK-BR-3 that exhibits a staining result of 3+, were provided as a marker standard substance that serves as a reference for the suitability of the marker detection results.

Specifically, control cell embedded blocks, in which each of the above-described cell lines was embedded in the embedding agent consisting of paraffin, were respectively prepared, and each of the control cell embedded blocks was hollowed out into a columnar shape using BIOPSY PUNCH (manufactured by Kai Industries Co., Ltd.) to obtain four types of marker standard substances.

(7-3-2) Preparation of Embedded Block Containing Marker Standard Substance

In order to prepare an embedded tissue section for verification in which the tissue section 42 is not embedded, here, the embedded block-preparing cassette 1 was placed on the tray 30 without placing the biological tissue fragment on the tray bottom 34. Each of the marker standard substances 21b, 21c, 21d, and 21e was inserted into each of the positioning holes 5a in the embedded block-preparing cassette 1, and then liquefied paraffin was poured thereto from the opening 4 of the embedded block-preparing cassette 1. After the paraffin was cooled and solidified, the embedded block-preparing cassette 1 was removed from the tray 30, and an embedded block in which the four types of marker standard substances 21b, 21c, 21d, and 21e were embedded in the same embedding agent was obtained.

(7-3-3) Preparation of Embedded Tissue Section for Verification

The embedded block in which only the four types of marker standard substances 21b, 21c, 21d, and 21e were embedded was set in the microtome (manufactured by Yamato Kohki Industrial Co., Ltd.), the embedded block was sliced while the slicing thickness was 2 μm, 3 μm, 4 μm, and 5 μm, and five embedded tissue sections for verification were prepared for each thickness. The marker standard substance sections 41d, 41c, 41b, and 41a were exposed on both surfaces of the embedded tissue sections for verification. In addition, the embedded tissue sections for verification were attached to one slide glass (manufactured by Matsunami Glass Industrial Co., Ltd.) one by one.

(7-3-4) Preparation of Calibration Curve for Evaluating Whether or not Detection is Suitable In the same manner as in the verification experiment 1, the height of the embedding agent section of the embedded tissue section was measured. After calculating the thickness of the embedding agent section for each embedded tissue section, a deparaffinization treatment, an antigen retrieval treatment, and an immunohistochemical staining treatment were performed by using Histofine HER2 Kit (POLY) (manufactured by Nichirei Biosciences Inc.). In order to prevent the marker standard substance section from drying over time, a mounting medium was dropped onto the slide glass to cover the marker standard substance sections 41d, 41c, 41b, and 41a with a cover glass.

By using a microscope (manufactured by Carl Zeiss, Axio Imager.Z2) provided with a digital camera (manufactured by Canon Inc., EOS-1D), three pieces of still image of each of the slides of the marker standard substance sections 41d, 41c, 41b, and 41a were respectively photographed (photographing conditions: objective lens magnification: 40 times, aperture: 0.90, shutter speed: 1/125, ISO: 800, LED: 19.9%, WB correction: A9/G9).

Based on the photographed still images, the staining intensities of the four types of marker standard substance sections 41d, 41c, 41b, and 41a were respectively scored based on the color tone of the marker standard substance sections 41d, 41c, 41b, and 41a. Specifically, by using a measurement program (manufactured by Canon Inc.), pixels of a predetermined color tone (a color tone having a hue of 50° to 180°, a chroma range of 2 to 40, an R value of 10 to 180, a G value of 10 to 145, and a B value of 10 to 140) were extracted from the still images of the marker standard substance sections 41d, 41c, 41b, and 41a, and the color tone was scored using the above-described Formula (1). Scoring was performed on all of the marker standard substance sections 41d, 41c, 41b, and 41a.

Figure 11:
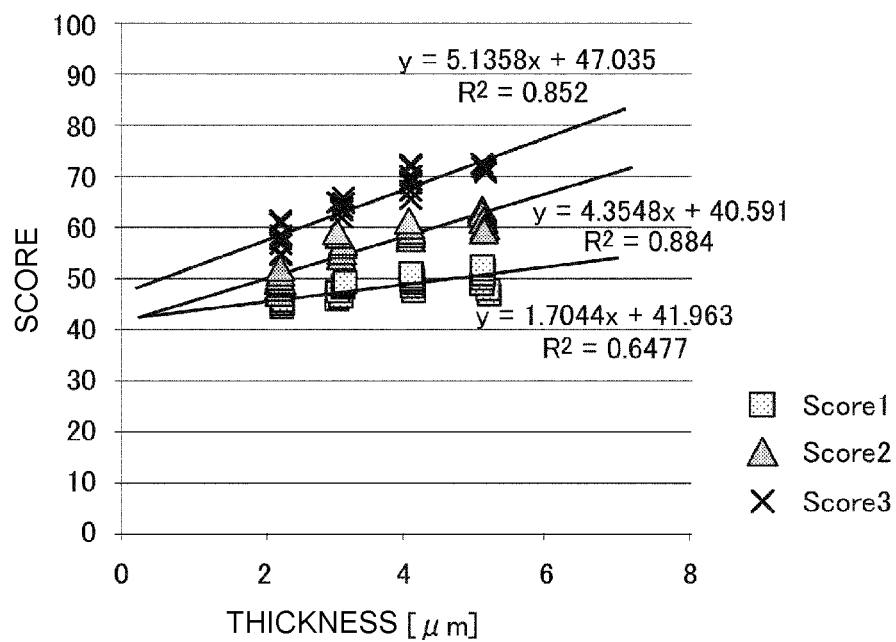
FIG. 11 is a graph illustrating a calibration curve that represents a relationship between a thickness of the tissue section and a staining intensity of a marker standard substance.

As illustrated in FIG. 11, the results were plotted, wherein a horizontal axis indicates the thickness of the tissue section (average height value of the embedding agent section) and a vertical axis indicates the staining intensity score. In addition, for each of the marker standard substance sections 41d, 41c, 41b, and 41a, a linear approximate equation was calculated by the least squares method based on the plot, and this was regarded as a calibration curve. Incidentally, the negative marker standard substance section 41d was not stained and thus is not illustrated in FIG. 11. In the drawing, Score 1 corresponds to the marker standard substance section 41c, Score 2 corresponds to the marker standard substance section 41b, and Score 3 corresponds to the marker standard substance section 41a. As illustrated in FIG. 11, by the linear approximate equation calculated by the least squares method, it was possible to prepare a calibration curve having a high correlation coefficient.

Each calibration curve illustrated in FIG. 11 represents a staining intensity score based on the color tones of the marker standard substance sections 41c, 41b, and 41a when the tissue section is appropriately stained. Therefore, by plotting the thickness of the tissue section and the staining intensity score of the marker standard substance sections 41c, 41b, and 41a on the graph illustrating the calibration curve, it is possible to see whether the difference between the plot and the calibration curve is within an appropriate range. Accordingly, it is possible to confirm whether or not the tissue section is appropriately stained by the calibration curve, and to select the tissue section to be inspected. In this manner, it was possible to confirm that the calibration curve that represents the relationship between the thickness of the tissue section and the staining intensity scores of the marker standard substance sections 41c, 41b, and 41a could be an index for selecting the tissue section to be inspected.

Figure 12:
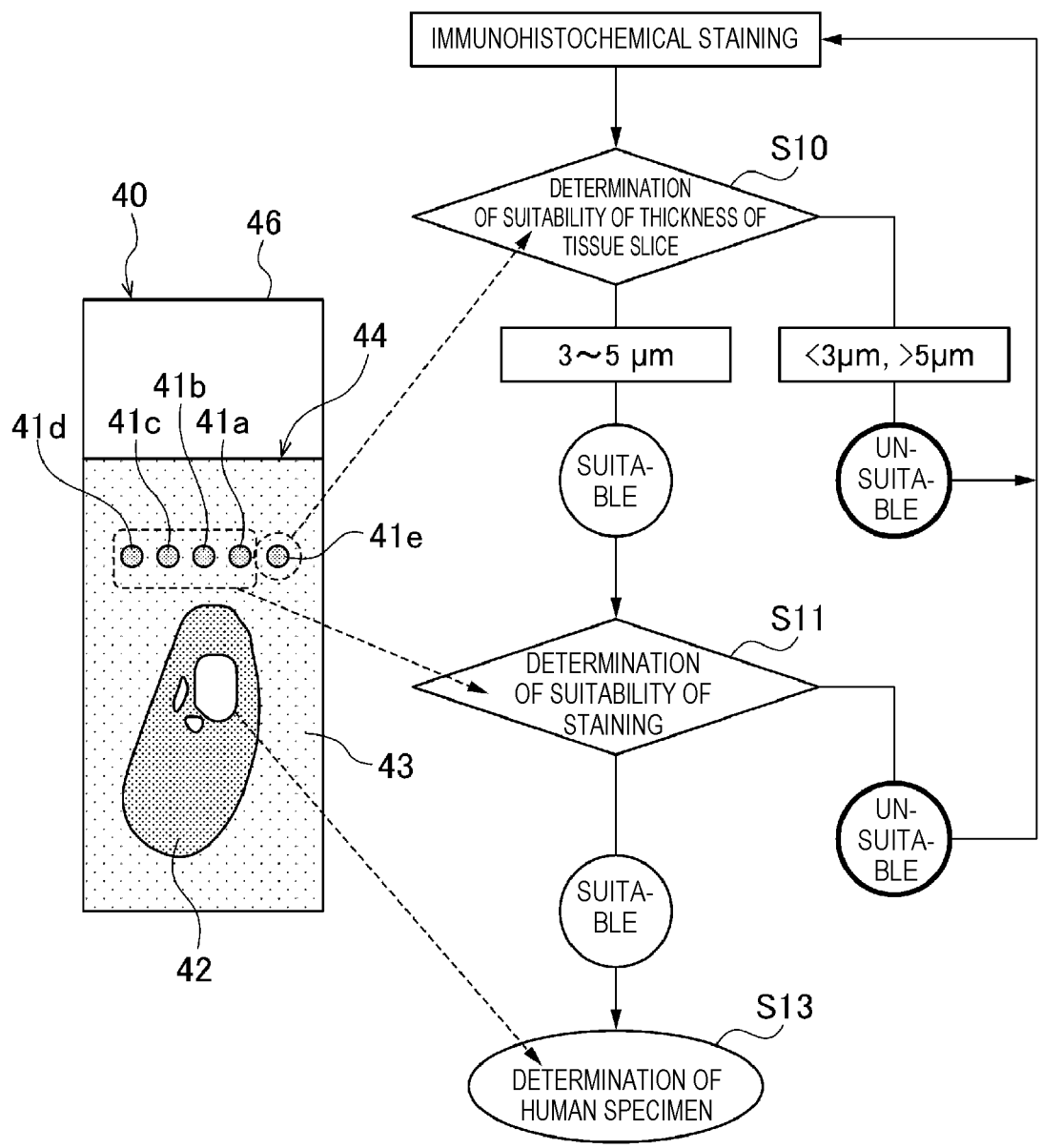
FIG. 12 is a schematic view for explaining a series of work (1) in an immunohistochemical staining method using the tissue section selection method.

(8) Immunohistochemical Staining Method Using Tissue Section Selection Method (8-1) Series of Work Using Tissue Section Selection Method of Present Invention Next, regarding the immunohistochemical staining method using the above-described tissue section selection method, a flow of a series of work will be briefly described with reference to FIG. 12. As illustrated in FIG. 12, in the immunohistochemical staining method, first, by using the embedded block-preparing cassette 1 illustrated in FIG. 1, the embedded block 24 in which both the biological tissue fragment 22 and the standard substance 21 are embedded in the same embedding agent 23 is prepared as illustrated in FIG. 4B.

Then, the embedded block-preparing cassette 1 integrated with the embedded block 24 is set on the microtome, and the embedded block 24 is sliced by the microtome set to a desired slicing thickness (for example, 4 μm) to obtain a sheet-like embedded tissue section 44. Thereafter, as illustrated on a left side in FIG. 12, a tissue section-mounting board 40 in which the embedded tissue section 44 is stretched and mounted on the board 46, such as, for example, a slide glass, is prepared.

In the tissue section-mounting board 40 thus prepared, the tissue section 42, the thickness standard substance section 41e as the standard substance section, and the marker standard substance sections 41d, 41c, 41b and 41a as the same standard substance sections are exposed on the surface of the embedding agent section 43.

Next, for example, the above-described embedding agent removing treatment, the protease treatment and the endogenous peroxidase treatment are sequentially performed. Thereafter, as the staining treatment by the immunohistochemical staining method, for example, after causing an antigen antibody reaction in the tissue section 42 using a primary antibody bound to the HER2/neu protein in the tissue section 42, a secondary antibody labeling polymer is bound to the primary antibody, and the HER2/neu protein contained in the tissue section 42 is stained further using a chromogenic reagent or the like to specifically detect the HER2/neu protein.

Next, the process proceeds to step S10 illustrated in FIG. 12, and based on the color tone of the thickness standard substance section 41e, suitability of the thickness of the tissue section 42 is determined. For the determination of the suitability of the thickness of the tissue section in step S10, for example, an image obtained by photographing the surface of the thickness standard substance section 41e is obtained with a microscope provided with a digital camera, pixels having a predetermined color tone are extracted from the image of the thickness standard substance section 41e by using the measurement program, and then the color tone is scored using the above-described Formula (1).

In addition, from the calibration curve that represents a relationship between the score of the thickness standard substance section 41e and the thickness, the thickness that corresponds to the score calculated by the above-described Formula (1) is specified, and this thickness is regarded as the thickness of the tissue section 42. As a result, when the thickness of the tissue section 42 is within a predetermined range (for example, 3 to 5 µm), it is determined that the thickness of the tissue section 42 is a thickness appropriate for the inspection, and the process proceeds to the next step S11.

Meanwhile, when the thickness of the tissue section 42 is out of the predetermined range (a thickness that corresponds to a score of less than 3 µm (<3 µm), or a thickness that corresponds to a score of more than 5 µm (>5 µm)), it is determined that the thickness of the tissue section 42 is a thickness inappropriate for the inspection, and thus the tissue section 42 is not inspected. The above-described immunohistochemical staining is performed on the other tissue section-mounting board 40, and then, the same treatment as those described above is performed. This process flow is repeated until the tissue section 42 having a predetermined thickness is obtained.

When it is determined that the tissue section 42 has a thickness appropriate for the inspection based on the color tone of the thickness standard substance section 41e, it is determined in step S11, for example, whether or not staining of the HER2/neu protein in the tissue section 42 is appropriately performed, based on the color tone of the marker standard substance section 41a.

For the determination as to whether or not staining is appropriately performed, for example, an image is obtained by photographing the surface of the marker standard substance section 41a with a microscope provided with a digital camera, and by using the measurement program, pixels having a predetermined color tone are extracted from the image of the marker standard substance section 41a, and the color tone is scored using the above-described Equation (1).

In addition, from the calibration curve that indicates a relationship between the staining intensity score of the marker standard substance section 41a and the thickness of the tissue section 42, and based on the thickness of the tissue section 42 calculated above and the staining intensity score of the marker standard substance section 41a, evaluation is effected as to whether or not the staining intensity score of the marker standard substance section 41a is within a predetermined range referring to the calibration curve.

As a result, when the staining intensity score is within a predetermined range with respect to the calibration curve, it is determined that the staining of the HER2/neu protein in the tissue section 42 is appropriate, and the process proceeds to the next step S13. On the other hand, when the staining intensity score deviates from the predetermined range with respect to the calibration curve, it is determined that the staining of the HER2/neu protein in the tissue section 42 is inappropriate, and inspection is not effected on the tissue section 42. And the above-described immunohistochemical staining is performed on the other tissue section-mounting board 40 and then, a treatment similar to those described above is performed. In this manner, the process flow of the immunohistochemical staining, step S10 and step S11 is repeated until a tissue section 42 having a predetermined staining intensity is obtained.

In step S13 (determination of human specimen), with respect to the tissue section 42 in which the staining of the HER2/new protein is determined to be appropriate, the operator compares the color tone of the tissue section 42 with the color tone of the marker standard substance sections 41d, 41c, 41b and 41a, and the tissue section 42 is inspected.

(8-2) Verification Experiment 4

Here, a verification experiment was performed, wherein a series of operation illustrated in FIG. 12 was actually performed continuously, and the thickness of the tissue section and the staining intensity score of the marker standard substance section were examined and compared with the calibration curve of "Score 3" illustrated in FIG. 11. Here, similar to the verification experiment 1, the blue pigment-containing urethane foam was used as the thickness standard substance, and the marker standard substance 21e made from the cell line SK-BR-3 showing a staining result of 3+ was used as a marker standard substance that serves as a reference for the suitability of the marker detection result.

The embedded block in which the thickness standard substance 21a and the marker standard substance 21e were embedded was set in the microtome (manufactured by Yamato Kohki Industrial Co., Ltd.), and the embedded block was sliced while setting the slicing thickness to 4 µm to give five embedded tissue sections for verification. The thickness standard substance section 41e and the marker standard substance section 41a were exposed on both surfaces of the embedded tissue section for verification. In addition, the embedded tissue sections for verification were attached one by one to a slide glass (manufactured by Matsunami Glass Industrial Co., Ltd.).

Next, a deparaffinization treatment, an antigen retrieval treatment, and an immunohistochemical staining treatment were performed by using Histofine HER2 Kit (POLY) (manufactured by Nichirei Biosciences Inc.). In order to prevent the marker standard substance section 41a from drying over time, a mounting medium was dropped onto the slide glass to cover the marker standard substance section 41a with a cover glass.

Next, the above-described slide glass was placed on the stage of the microscope (manufactured by Carl Zeiss) provided with a digital camera (manufactured by Canon Inc., EOS-1D), and the surface of the thickness standard substance section 41e was photographed by focusing on the surface of the thickness standard substance section 41e.

Accordingly, an image of the thickness standard substance section 41e was obtained (photographing conditions: objective lens magnification: 2.5 times, shutter speed: 1/250, ISO: 800, LED: 19.9%, WB correction: A9/G9).

Based on the image of the thickness standard substance section 41e, the color tone of the thickness standard substance section 41e was scored using a measurement program (manufactured by Canon Inc.). Specifically, by using the measurement program, the pixels of the color tone in a hue range of 272° to 305°, a chroma range of 0 to 51, a brightness range of a R value of 0 to 71, a brightness range of a G value of 0 to 77, and a brightness range of a B value of 0 to 77 were extracted from the image of the thickness standard substance section 41e, and the color tone was scored by using the above-described Formula (1). In addition, based on the obtained score, the height of the thickness standard substance section 41e was measured from the calibration curve illustrated in FIG. 9.

In addition, using a microscope (manufactured by Carl Zeiss, Axio Imager.Z2) provided with a digital camera (manufactured by Canon Inc., EOS-1D), slides of the still images of the marker standard substance section 41a were respectively photographed (photographing conditions: objective lens: 40 times, aperture: 0.90, shutter speed: 1/125, ISO: 800, LED: 19.9%, WB correction: A9/G9).

Based on the photographed still image, the staining intensity of the marker standard substance section 41a was scored based on the color tone of the marker standard substance section 41a. Specifically, by using the measurement program (manufactured by Canon Inc.), pixels of a predetermined color tone (a color tone in a hue range of 50° to 180°, a chroma range of 2 to 40, an R value of 10 to 180, a G value of 10 to 145, and a B value of 10 to 140) were extracted from the still image of the marker standard substance section 41a, and the color tone was scored using the above-described Formula (1).

Figure 13:
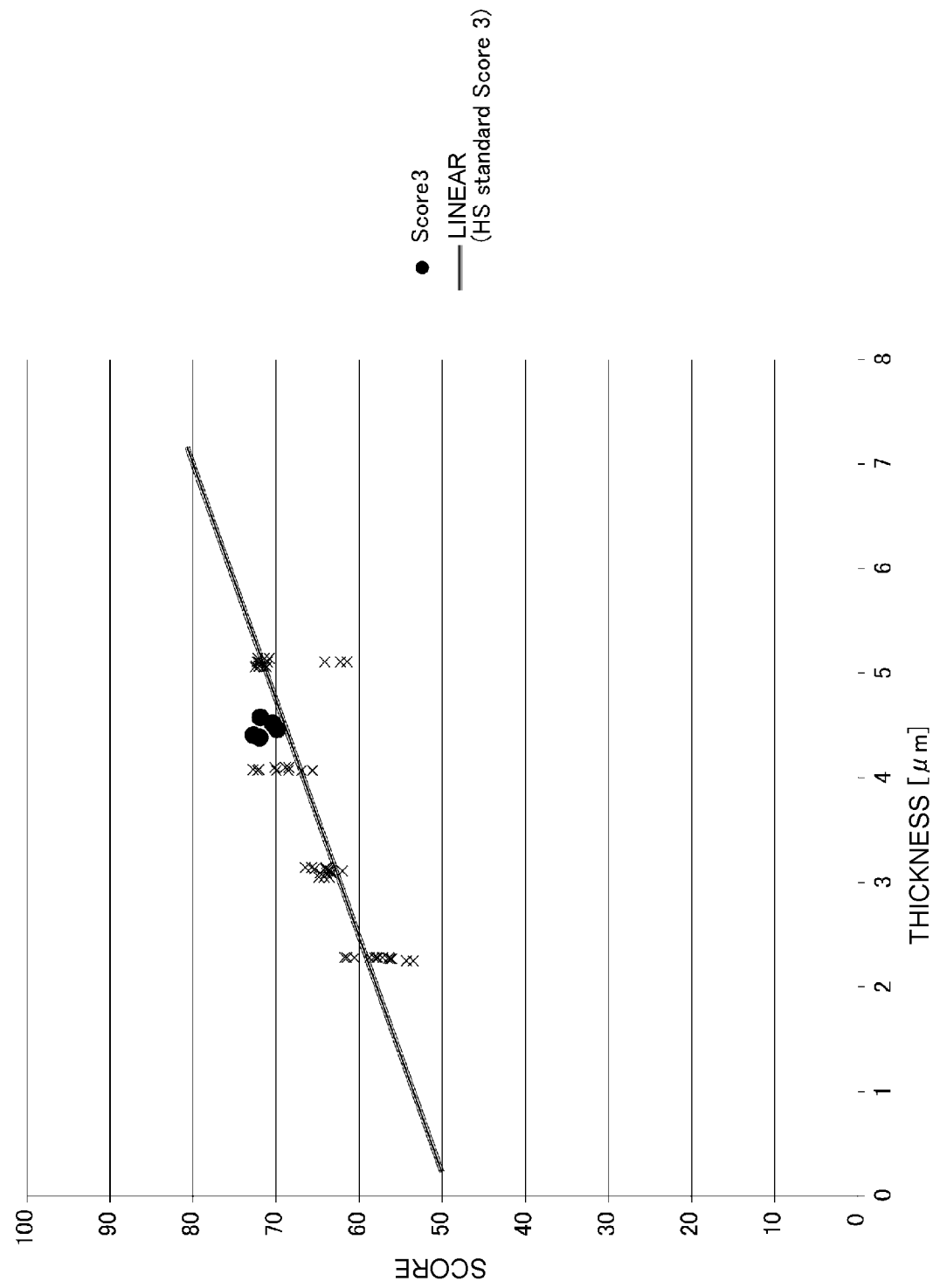
FIG. 13 is a graph illustrating results of examining a thickness of a tissue section and a staining intensity score of a marker standard substance section and plotting them with respect to a calibration curve.

In addition, as illustrated in FIG. 13, the measurement result of each embedded tissue fragment for verification was plotted, wherein a horizontal axis indicates the thickness of the thickness standard substance section 41e, and a vertical axis indicates the staining intensity score, and the result was compared with the calibration curve of "Score 3" illustrated in FIG. 11. Incidentally, the "linear (HS standard Score 3)" in FIG. 13 indicates a calibration curve of "Score 3" in FIG. 11. As a result of the comparison, the difference between the plot and the calibration curve was within an appropriate range, and it was possible to confirm whether or not the tissue section was appropriately stained in any of the embedded tissue sections for verification by the calibration curve. Accordingly, it was confirmed that it was possible to select the tissue section to be inspected by the tissue section selection method of the present invention.

(9) Immunohistochemical Staining Method Using Tissue Section Selection Method for Determining Fixed State of Tissue Section (9-1) Preparation of Tissue Section-Mounting Board Here, different from the above-described embodiment, the tissue section selection method for determining the state of the fixed tissue section will be described below. In the embedded block-preparing step of preparing an embedded block, a biological (living) tissue fragment collected from the living body is usually immersed in a fixing solution such as a formalin aqueous solution for a predetermined period of time or more (immersing step). As a typical fixing solution, a 10% formalin aqueous solution (4% formaldehyde solution) obtained by diluting a formalin stock solution with distilled water or a buffer is known.

Here, an appropriate period of time for immersing the biological tissue fragment in the fixing solution depends on the fixing solution, the size of the biological tissue fragment or the like. For example, in a case of staining the HER2/neu protein, it is recommended to immerse the biological tissue fragment in the fixing solution for 6 to 72 hours by using the above-described 10% formalin aqueous solution (the period of time for immersing the biological tissue fragment in the fixing solution is referred to as a fixing time). By immersing the biological tissue fragment in the fixing solution for the recommended fixing time, it is possible to optimally fix the tissue form or the antigen activity of the biological tissue fragment by the fixing solution.

In this manner, after the biological tissue fragment is immersed in the fixing solution for a predetermined period of time, the biological tissue fragment is placed at a predetermined position on the tray (placing step). In addition, the embedded block-preparing cassette is placed on the tray, and a liquid embedding agent such as paraffin that is liquefied by heating is poured from the embedded block-preparing cassette onto the tray (liquid embedding agent introducing step).

The liquid embedding agent is poured until the biological tissue fragment on the tray is covered (liquid embedding agent introducing step), and by cooling and solidifying the liquid embedding agent, the biological tissue fragment is embedded in the embedding agent, and an embedded block integrated with the embedded block-preparing cassette can be prepared (solidifying step).

In addition, the embedded block-preparing cassette integrated with the embedded block is set in the microtome, the embedded block is sliced by the microtome set to a desired slicing thickness (for example, 4 μm), and the sheet-like embedded tissue section is obtained.

Figure 14:
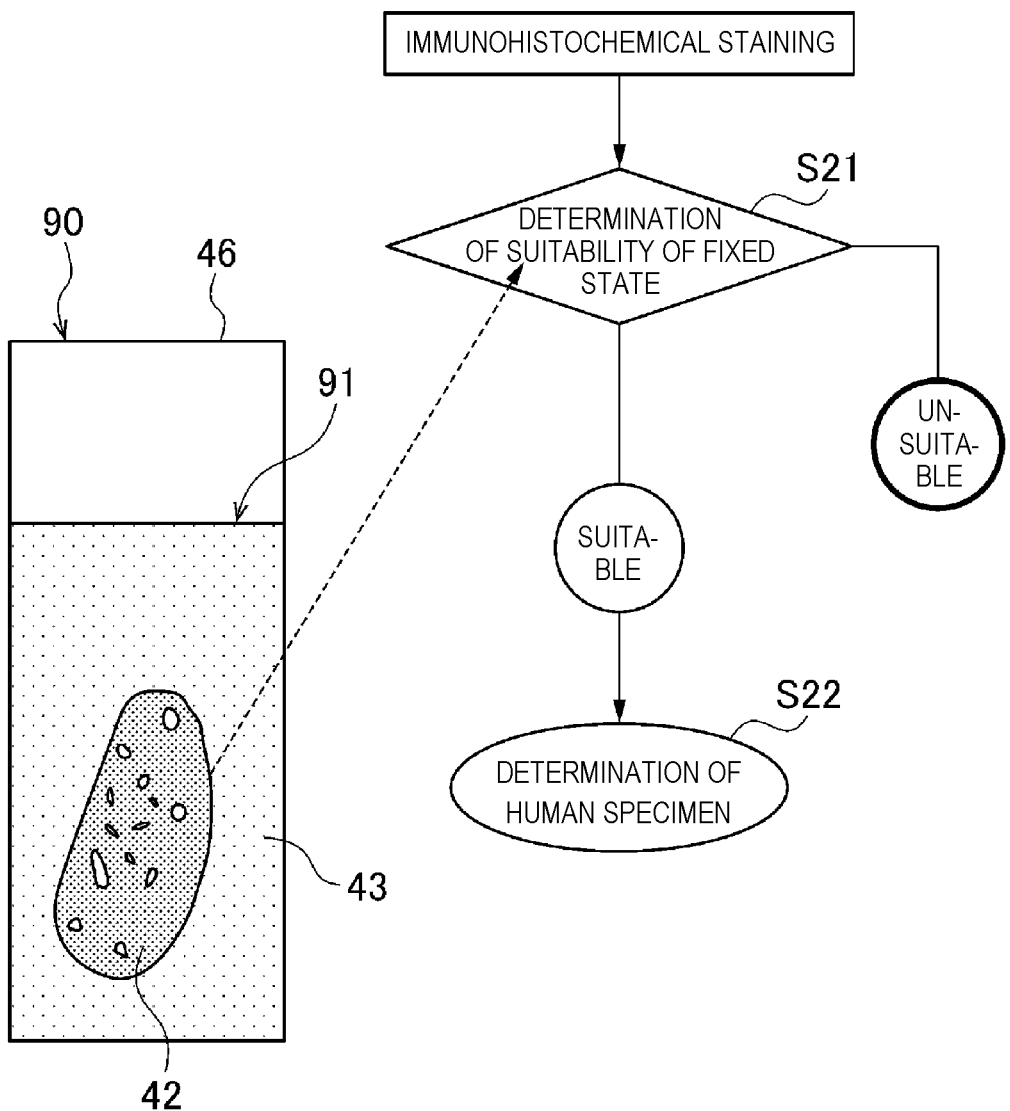
FIG. 14 is a schematic view for explaining a series of work (2) in an immunohistochemical staining method using the tissue section selection method.

Thereafter, as illustrated in the left side of FIG. 14, for example, by stretching and mounting the embedded tissue section 91 on the substrate 46 such as a slide glass, a tissue section-mounting board 90 is prepared. Incidentally, the embedded tissue section 91 of the present embodiment has a configuration in which the tissue section 42 is exposed on the surface and the circumference of the tissue section 42 is surrounded by the embedding agent section 43.

(9-2) Determination Method of Fixed State of Tissue Section

Here, when preparing the embedded block, a fixing treatment for fixing the biological tissue fragment obtained from the living body is performed to give an optimal state as to the tissue form and the antigen activity. However, if, for example, the period of time for immersing the biological tissue fragment in the fixing solution is not sufficient, the biological tissue fragment is unlikely to be optimally fixed. When the biological tissue fragment is not optimally fixed, the tissue form and the antigen activity of the biological tissue fragment are not maintained, and then when inspecting the tissue section prepared from the biological tissue fragment by the immunohistochemical staining therafter, the tissue sections are unlikely to be stained, and there is a possibility that an error occurs in the inspection results.

Here, in the present embodiment, it is determined with respect to the tissue section-mounting board 90 as to whether or not the state of the tissue section 42 fixed by the fixing solution is optimal. In this case, a staining treatment is performed on the embedded tissue section 91 by an immunohistochemical staining, and based on the light signal from the endogenous protein expressed in the cells in the tissue section 42, it is determined whether or not the state of the tissue section 42 fixed by the fixing solution is optimal. Hereinafter, the determination method of the state of the fixed tissue section 42 will be described.

In the present embodiment, for example, different from the staining treatment by the immunohistochemical staining method for staining the HER2/neu protein of the tissue section 42, another staining treatment by the immunohistochemical staining method is performed on the tissue section-mounting board 90, and an endogenous protein expressed in the cells in the tissue section 42 is stained. Here, the color tone at the time of staining of the endogenous protein on which the staining treatment by the immunohistochemical staining method is performed changes corresponding to the state of the biological tissue fragment fixed by the fixing solution which was performed when the embedded block was prepared. Based on the color tone of the endogenous protein contained in the tissue section 42, the operator determines whether or not the fixing treatment on the tissue section 42 has been appropriately performed.

Here, the endogenous protein contained in the tissue section and used in the determination method is desirably endogenous protein in which an expression level does not substantially change depending on the cell, or endogenous protein stably expressed at an evaluated position. For example, this type of endogenous protein is desirably CD34 detected in capillary endothelial cells.

Since capillary blood vessels are generally present in the biological tissue fragments that are inspected for the presence or absence of tumor cells, such as breast cancer, the CD34 detected in the capillary endothelial cells is also stably expressed. In addition, since it is known that angiogenesis is generally accelerated around tumors, it can be said that in a case where there are tumor cells in the biological tissue fragment, the CD34 detected in the capillary endothelial cells is stably expressed.

In a case where the CD34 is applied as the endogenous protein expressed in the cells in the tissue section, an anti-CD34 antibody can be applied as an anti-endogenous protein antibody that stains the endogenous protein. As the anti-CD34 antibody, for example, the anti-CD34 rabbit polyclonal antibody can be applied.

When more specifically the above-described treatment steps are described, in the present embodiment, after obtaining the tissue section-mounting board 90, for example, the above-described embedding agent removing treatment, the protease treatment, and the endogenous peroxidase treatment are sequentially performed. Thereafter, as the staining treatment by the immunohistochemical staining method, for example, after causing an antigen-antibody reaction in the tissue section 42 using a primary antibody that binds to the HER2/neu protein in the tissue section 42, a secondary antibody-labeled polymer is bound to the primary antibody, and the HER2/neu protein contained in the tissue section 42 is stained further using a chromogenic reagent or the like to specifically detect the HER2/neu protein.

In addition, at this time, as another staining treatment by the immunohistochemical staining method, further, after causing an antigen-antibody reaction in the tissue section 42 using a primary antibody that binds to the endogenous protein expressed in the cells in the tissue section 42, the secondary antibody-labeled polymer is bound to the primary antibody, and the endogenous protein contained in the tissue section 42 is stained further using a chromogenic reagent or the like to specifically detect the endogenous protein.

In this case, by changing the color tone of the HER2/neu protein contained in the tissue section 42 when it is stained and the color tone of the endogenous protein contained in the tissue section 42 when it is stained, it is possible to distinguish staining state of the HER2/neu protein from that of the endogenous protein.

Further, in a case of staining the HER2/neu protein contained in the tissue section 42, it is confirmed by the verification experiment that, for example, the CD34 can be used as the endogenous protein used for evaluating the fixing state of the tissue section 42. It has been confirmed that it is possible to avoid overlapping of the color tone of the stained HER2/neu protein and the color tone of the stained CD34 in a case where the CD34 is applied in the determination of the fixing state. Therefore, based on the color tone of the CD34 contained in the tissue section 42, the operator can determine whether or not the fixing treatment for the tissue section 42 has been appropriately performed.

Here, a flow of a series of operation will be briefly described with reference to FIG. 14 regarding the immunohistochemical staining method using the tissue section selection method in the present embodiment. As illustrated in FIG. 14, in the immunohistochemical staining method herein, a staining treatment for staining the HER2/neu protein contained in the tissue section 42 and a staining treatment for staining the endogenous protein contained in the tissue section 42 are respectively performed with respect to the tissue section-mounting board 90, and the process proceeds to step S21.

In step S21, the state of the tissue section 42 fixed is determined based on the staining intensity of the endogenous protein that is contained in the tissue section 42 and changed by the staining treatment. Incidentally, in the determination of the fixed state of the tissue section 42, for example, an image obtained by photographing the surface of the tissue section 42 is obtained using the microscope provided with a digital camera, and by using a measurement program, pixels having a predetermined color tone are extracted from the image of the tissue section 42, and the color tone is scored using the above-described Formula (1).

Figure 15:
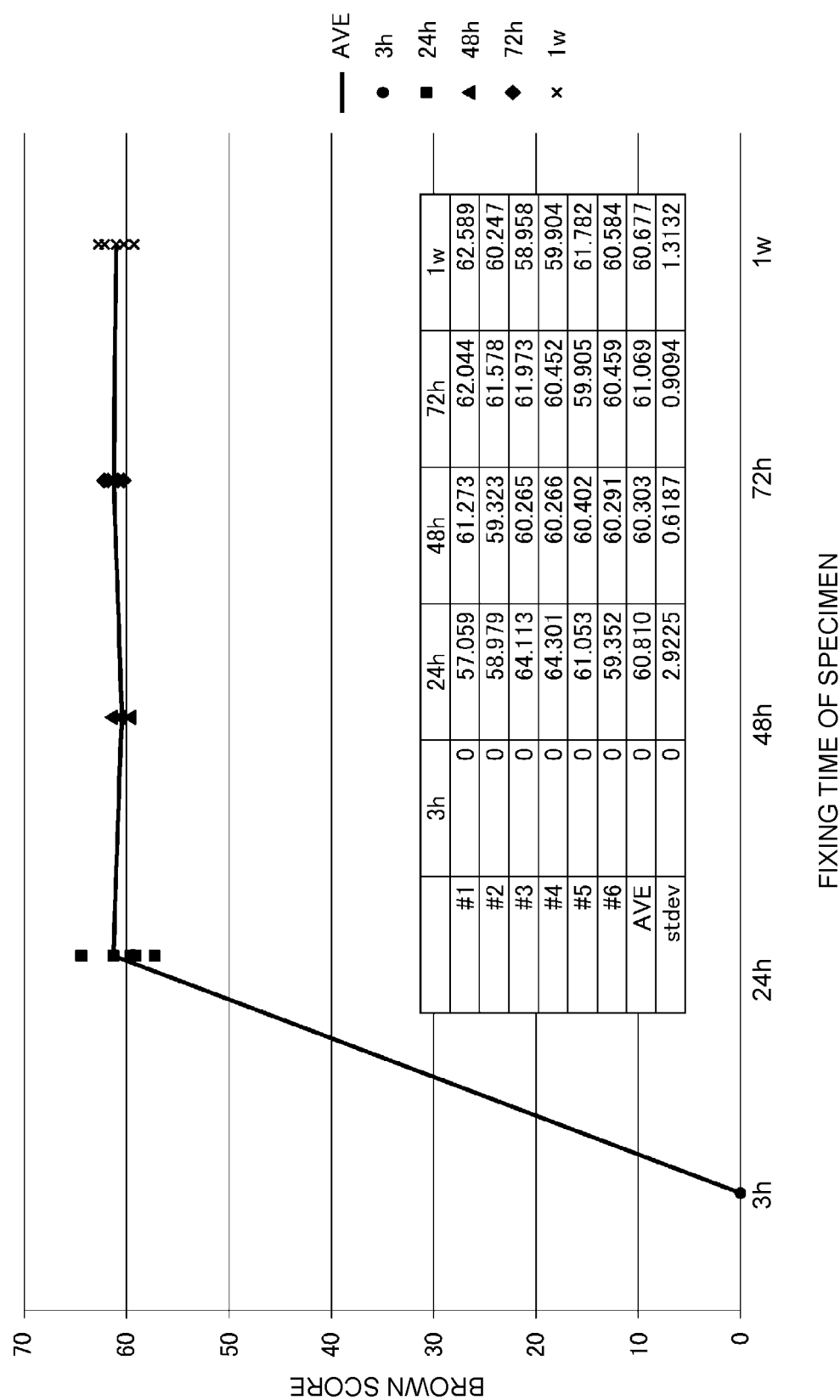
FIG. 15 is a graph illustrating a relationship between a specimen fixing time and a brown score.

Here, as illustrated in FIG. 15, a graph (which will be described later) that represents a relationship between the score obtained from the color tone of the endogenous protein and the fixing time is prepared in advance. From the graph, a fixing time that corresponds to the score calculated by the above-described Equation (1) is calculated, and this value can be estimated as the fixing time of the tissue section 42. As a result, when the fixing time of the tissue section 42 is equal to or longer than a predetermined time (for example, 24 hours or longer), the fixing time at the time of the fixing treatment performed on the tissue section 42 is optimal, and it is determined that the tissue section 42 is in a fixing state appropriate for the inspection. Then the process proceeds to the next step S22.

Meanwhile, when the fixing time of the tissue section 42 obtained from the graph is shorter than the predetermined period of time (when the fixing time that corresponds to the score is shorter than, for example, 24 hours), the fixing time for the tissue section 42 is insufficient, and it is determined that the tissue section is in a fixing state inappropriate for the inspection. Then the determining treatment is terminated without inspecting the tissue section 42.

In step S21, when the tissue section 42 to be an inspection target is selected based on the color tone of the endogenous protein contained in the tissue section 42, the operator, in step S22 (human specimen determination), compares the color tone of the HER2/neu protein in the tissue section 42 with the control slide prepared in advance, and inspects whether or not the HER2/neu protein is present in the tissue section 42.

(9-3) Action and Effects

In the tissue section selection method according to the present embodiment with the above-described configuration, the biological tissue fragment is immersed in a fixing solution for a predetermined time, and then the biological tissue fragment is embedded in an embedding agent to prepare the embedded block (embedded block-preparing step). Further, the embedded block is sliced to prepare the sheet-like embedded tissue section 91 in which the tissue section 42 appears on the surface (embedded tissue section-preparing step).

In the tissue section selection method, when the marker is specifically detected and the tissue section 42 is selected as an inspection target, the staining treatment is performed on the embedded tissue section 91 to stain the endogenous protein expressed in the cells in the tissue section 42. Thus, based on the light signal from the endogenous protein expressed in the cells in the tissue section 42, the state of the tissue section 42 fixed with the fixing solution is determined (fixing state determining step).

In other words, in the tissue section selection method according to the present embodiment, the fixing time of the tissue section 42 is estimated from the color tone of the endogenous protein contained in the tissue section 42. Accordingly, in the tissue section selection method, only the tissue section 42 having an optimum fixing state for the inspection can be selected, and thus inspection can be performed only on the selected tissue section 42. Accordingly, it is possible to suppress occurrence of an error in the inspection result.

(9-4) Modification Example

Incidentally, the present invention is not limited to the above-described embodiment, and various modifications can be made within the scope of the gist of the present invention. While above-described embodiment describes a case where both the staining treatment for staining the HER2/neu protein in the tissue section 42 and the staining treatment for staining the endogenous protein expressed in the cells in the tissue section 42 are performed by the immunohistochemical staining method, the present invention is not limited thereto. For example, only the staining treatment for staining the endogenous protein expressed in the cells in the tissue section 42 may be performed. Further, after the fixing state determining step of determining the fixing state of the tissue section 42, for example, the staining treatment by the immunohistochemical staining method for staining the HER2/neu protein in the tissue section 42 may be performed.

Furthermore, for example, the fixing state determining step for determining the fixing state of the tissue section 42 according to the present embodiment may be incorporated in the above-described "(8) Immunohistochemical Staining Method Using Tissue Section Selection Method".

In this case, the step can be realized by providing the fixing state determining step illustrated in step S21 of FIG. 14 after the embedded tissue section preparing step of preparing the sheet-like embedded tissue section, before step S10 (tissue section thickness determining step) in the flowchart illustrated in FIG. 12, or after step S10 (tissue section thickness determining step), or after step S11 (marker suitability determining step).

More specifically, for example, by providing the step S21 of FIG. 14 after performing the staining treatment for staining the HER2/neu protein in the tissue section 42 and the staining treatment for staining the endogenous protein expressed in the cells in the tissue section 42 by the immunohistochemical staining method, before step S10, or after step S10, or after step S11 illustrated in FIG. 12, the fixing state of the tissue section 42 can be determined.

Further, the tissue section selection method may be such a method in which the following steps are combined: (i) the tissue section thickness determining step for determining the thickness of the tissue section 42 based on the color tone of the thickness standard substance section 41e as illustrated in step S10 in FIG. 12, and (ii) the fixing state determining step for determining the fixing state of the tissue section 42 fixed by a fixing solution based on the color tone of the endogenous protein in the tissue section changed by another staining treatment as illustrated in step S21 in FIG. 14.

In this case, by using a tissue section-mounting board on which the tissue section 42 and the thickness standard substance section 41e as the standard substance section are exposed on the surface of the embedding agent section 43, the above-described step S10 and step S21 are performed.

Further, the tissue section selection method may be such a method in which the following steps are combined: (i) the marker suitability determining step for determining whether or not staining of the HER2/neu protein in the tissue section 42 is appropriately performed based on the color tone of the marker standard substance section 41a, as illustrated in step S11 in FIG. 12, and (ii) the fixing state determining step for determining the state of the tissue section 42 fixed by the fixing solution based on the color tone of the endogenous protein in the tissue section changed by another staining treatment, as illustrated in step S21 in FIG. 14.

In this case, the above-described step S11 and step S21 are performed by using the tissue section-mounting board on which the tissue section 42 and the marker standard substance sections 41d, 41c, 41b and 41a as the standard substance section are exposed on the surface of the embedding agent section 43.

(9-5) Verification Experiment 5

(9-5-1) Examination of Concentration of Anti-CD34 Rabbit Polyclonal Antibody In verification experiment 5, a porcine mammary gland tissue was prepared, and the porcine mammary gland tissue was set in the microtome (manufactured by Yamato Kohki Industrial Co., Ltd.). The slicing thickness of the microtome was set to 4 μm, and the porcine mammary gland tissue was sliced to prepare a plurality of tissue sections for verification. After the tissue section for verification was attached to the slide glass (manufactured by Muto Glass Industrial Co., Ltd.), staining was performed on CD34 of the tissue section for verification with an anti-CD34 rabbit polyclonal antibody (Abcam Co.) having different concentrations.

As the anti-CD34 rabbit polyclonal antibodies with different concentrations, anti-CD34 rabbit polyclonal antibodies were diluted with PBS to prepare an antibody with a concentration of 1/100, an antibody with a concentration of 1/200, an antibody with a concentration of 1/400, an antibody with a concentration of 1/800, and an antibody with a concentration of 1/1600. In addition, the staining treatment for staining the porcine mammary gland tissue was performed using the five types of antibodies having different concentrations.

Next, the tissue section for verification after the staining treatment was encapsulated in a slide glass, and the slide glass was placed on the stage of the microscope (manufactured by Carl Zeiss) provided with a digital camera (manufactured by Canon Inc., EOS-1D), and the surface of the tissue section for verification was photographed by focusing on the surface of the tissue section for verification. Accordingly, images 93a, 93b, 93c, 93d, and 93e illustrated in FIG. 16 were respectively obtained (photographing conditions: shutter speed: 1/250, ISO: 800, WB correction A9/G9, LED: 19.9%, aperture: 0.50, objective lens magnification: 40 times).

The image 93a is an image obtained by photographing the surface of the tissue section for verification which was stained using the antibody having a concentration of 1/100, the image 93b is an image obtained by photographing the surface of the tissue section for verification which was stained using the antibody having a concentration of 1/200, the image 93c is an image obtained by photographing the surface of the tissue section for verification which was stained using the antibody having a concentration of 1/400, the image 93d is an image obtained by photographing the surface of the tissue section for verification which was stained using the antibody having a concentration of 1/800, and the image 93e is an image obtained by photographing the surface of the tissue section for verification which was stained using the antibody having a concentration of 1/1600.

Further, as a negative control, the same porcine mammary gland tissue as described above was prepared as the tissue section for verification, and similarly, the tissue section for verification was photographed to acquire an image 93f.

From the results illustrated in FIG. 16, in the tissue sections for verification on which the staining was performed using the antibody having a concentration of 1/100 and the antibody having a concentration of 1/200, it was possible to confirm that the color tone was deepened as illustrated in the images 93a and 93b. As described above, in a case where the color tone is deepened, for example, in a case where the HER2/neu protein or the like is further stained, there is a concern that the staining may also be affected. Therefore, it is desirable to use an antibody with a concentration lower than 1/200.

Meanwhile, in the tissue section for verification on which the staining was performed using an antibody having a concentration of 1/1600, the color tone was lightened, as illustrated in the image 93e, substantially similar to the image 93f of the negative control, and it was confirmed that the staining was insufficient. From the above, it was confirmed that the tissue section for verification was stained by using the anti-CD34 rabbit polyclonal antibody having a concentration of more than 1/200 and less than 1/1600, more preferably the antibody having a concentration of 1/400 or more and 1/800 or less.

(9-5-2) Evaluation of Staining Using Anti-CD34 Rabbit Polyclonal Antibody Regarding Fixing Time When Porcine Mammary Gland Tissue was Immersed in Fixing Solution Next, a verification experiment was performed on the case where a porcine mammary gland tissue section for verification was stained using the above-described antibody having a concentration of 1/400 in order to confirm whether or not the color tone changes depending on the difference in fixing time when the porcine mammary gland tissue is immersed in a fixing solution.

Here, a part of the porcine mammary gland tissue was excised to obtain a plurality of tissue blocks, and each of the tissue blocks immediately after excision was respectively immersed in a fixing solution. A 10% formalin aqueous solution was used as the fixing solution. In addition, the time for immersing the tissue block in the fixing solution (fixing time) was changed for each tissue block.

The fixing time of the tissue block was set to 3 hours, 24 hours, 48 hours, 72 hours, and 1 week. After each time has elapsed, each tissue block was sliced using the microtome (manufactured by Yamato Kohki Industrial Co., Ltd.) set at a slicing thickness of 4 μm, and the tissue sections for verification were prepared.

After the tissue section for verification was attached to the slide glass (manufactured by Muto Glass Industrial Co., Ltd.), staining was performed with respect to the CD34 of the tissue section for verification using the anti-CD34 rabbit polyclonal antibody (Abcam Co.) having a concentration of 1/400, respectively.

Next, the slide glass in which a staining-treated tissue section for verification was encapsulated was placed on the stage of the microscope (manufactured by Carl Zeiss) provided with a digital camera (manufactured by Canon Inc., EOS-1D), and the surface of the tissue section for verification was photographed by focusing on the surface of the tissue section for verification. Thus, images 94a, 94b, 94c, 94d, and 94e illustrated in FIG. 17 were obtained.

The image 94a is an image obtained by photographing the surface of the tissue section for verification with a fixing time of 3 hours, the image 94b is an image obtained by photographing the surface of the tissue section for verification with a fixing time of 24 hours, the image 94c is an image obtained by photographing the surface of the tissue section for verification with a fixing time of 48 hours, the image 94d is an image obtained by photographing the surface of the tissue section for verification with a fixing time of 72 hours, and the image 94e is an image obtained by photographing the surface of the tissue section for verification with a fixing time of 1 week.

From the image 94a, it was confirmed that sufficient staining was not obtained with respect to the tissue section for verification with a fixing time of 3 hours. Meanwhile, from the image 94b, it was confirmed that the tissue section for verification with a fixing time of 24 hours was stained. Further, from the images 94b, 94c, 94d, and 94e, it was confirmed that no significant difference was observed in staining among the cases where the fixing time was set in a range of from 24 hours to 1 week.

From the above, it was confirmed that there was a large difference in staining between the case where the fixing time was set to 3 hours and the case where the fixing time was set to 24 hours. Accordingly, it was confirmed that it is possible to determine the fixing time of the tissue section by the difference in color tone by staining the tissue section using the anti-CD34 rabbit polyclonal antibody having a concentration of 1/400.

(9-5-3) Preparation of Graph for Determining Suitability of Fixing State of Tissue Section Next, preparation of a graph (FIG. 15) for determining suitability of the fixing state of the tissue section will be described. Immediately after cutting out a plurality of tissue blocks from the porcine mammary gland tissue, each of the tissue blocks was immersed in the fixing solution. The fixing time of the tissue block was set to 3 hours, 24 hours, 48 hours, 72 hours, and 1 week. After each time has elapsed, each tissue block was sliced using the microtome (manufactured by Yamato Kohki Industrial Co., Ltd.) set at a slicing thickness of 4 μm, to give the tissue sections for verification.

The tissue sections for verification were attached to the slide glass (manufactured by Muto Glass Industrial Co., Ltd.). Two such slide glasses were respectively provided for each fixing time. The anti-CD34 rabbit polyclonal antibody (Abcam Co.) was diluted with PBS to prepare an antibody having a concentration of 1/400, and staining was performed on CD34 in each tissue section for verification using the antibody.

Next, the tissue section for verification after the staining treatment was encapsulated in a slide glass and the slide glass was placed on the stage of the microscope (manufactured by Carl Zeiss) provided with a digital camera (manufactured by Canon Inc., EOS-1D), and the surface of the tissue section for verification was photographed by focusing on the surface of the tissue section for verification. Images 98a, 98b, 98c, 98d, and 98e illustrated in FIG. 21, for example, were obtained with photographing conditions: shutter speed of 1/250, ISO of 800, WB correction of A9/G9, LED of 19.9%, aperture of 0.50, and objective lens of 40 times.

Incidentally, the image 98a is an image obtained by photographing the surface of the tissue section for verification with a fixing time of 3 hours, the image 98b is an image obtained by photographing the surface of the tissue section for verification with a fixing time of 24 hours, the image 98c is an image obtained by photographing the surface of the tissue section for verification with a fixing time of 48 hours, the image 98d is an image obtained by photographing the surface of the tissue section for verification with a fixing time of 72 hours, and the image 98e is an image obtained by photographing the surface of the tissue section for verification with a fixing time of 1 week. The image 98f is an image obtained by enlarging a part of the image 98c obtained by photographing the surface of the tissue section for verification with a fixing time of 48 hours.

Based on the obtained images 98a, 98b, 98c, 98d, and 98e, the stained portions stained to brown color were scored. Specifically, by using the measurement program (manufactured by Canon Inc.), for example, pixels of a predetermined color tone (thinning out of pixels in the image: 1/64, a chroma range: 12 to 25, a hue range: 90° to 120°, and RGB ranges: a R value of 85 to 130, a G value of 65 to 120, and a B value of 65 to 120) were extracted from each of the images 98a, 98b, 98c, 98d and 98e, and the color tone was scored using the above-described Formula (1).

As illustrated in FIG. 15, wherein a horizontal axis indicates a fixing time of the tissue section (specimen fixing time) and a vertical axis indicates a staining intensity score (brown score), the results are plotted to give a graph illustrated in FIG. 15.

As a result, as illustrated in FIG. 15, it was possible to express as a graph the staining intensity score based on the color tone of the tissue section when the fixing treatment was appropriately performed on the tissue section. Therefore, by plotting the staining intensity score obtained based on the tissue section in the graph, the fixing time can be estimated. Accordingly, it is possible to confirm whether or not the fixing treatment is appropriately performed on the tissue section by the graph, and to select the tissue section to be inspected. In this manner, it was possible to confirm that the graph that expresses a relationship between the staining intensity score of the tissue section and the fixing time could be an index for selecting the tissue section to be inspected.

REFERENCE SIGNS LIST

1 EMBEDDED BLOCK-PREPARING CASSETTE
2 BOX BODY
3 FRAME
4 OPENING
5 STANDARD SUBSTANCE-POSITIONING PORTION
6 THROUGH HOLE
21 STANDARD SUBSTANCE
42 TISSUE SECTION
43 EMBEDDING AGENT SECTION
44 EMBEDDED TISSUE SECTION

The invention claimed is:

1. A tissue section selection method for selecting a tissue section to be inspected by specifically detecting a marker, the method comprising:
(a) an embedded block-preparing step for preparing an embedded block by embedding both a biological tissue fragment and a standard substance in an embedding agent;
(b) an embedded tissue section-preparing step for preparing an embedded tissue section having a sheet shape by slicing the embedded block, the embedded tissue section having a tissue section and a standard substance section embedded in the embedding agent and appearing on the surface thereof; and
(c) a tissue section-selecting step for selecting the tissue section to be inspected by comparing a light signal from the standard substance section with a calibration curve as a reference, and selecting the tissue section to be inspected when the tissue section is determined to have a predetermined thickness, wherein
the standard substance comprises a thickness standard that serves as a reference for the thickness of the tissue section, and
the calibration curve represents a relationship between thickness of the tissue section and a color tone of the standard substance.

2. The tissue section selection method according to claim 1, wherein the embedded block-preparing step (a) includes:
(a-1) a placing step of placing the biological tissue fragment on a bottom of a tray;
(a-2) a positioning step comprising:
(i) providing an embedded block-preparing cassette,
(ii) inserting the thickness standard substance into a positioning hole in the embedded block-preparing cassette, and
(iii) positioning the thickness standard substance such that the thickness standard substance is present within a height range of from a lower end to an upper end of the biological tissue fragment when the bottom of the tray is taken as a reference;
(a-3) a liquid embedding agent-introducing step comprising:
(i) pouring a liquid embedding agent into the tray; and
(ii) a solidifying step comprising solidifying the liquid embedding agent to prepare the embedded block in which the biological tissue fragment and the thickness standard substance are embedded together in the embedding agent.

3. The tissue section selection method according to claim 1, wherein
the standard substance further comprises a marker standard substance that serves as a reference for suitability of a marker detection result.

4. The tissue section selection method according to claim 2, wherein
the standard substance further comprises a marker standard substance that serves as a reference for suitability of a marker detection result.

5. The tissue section selection method according to claim 1, wherein
the standard substance is made of a cell which expresses an endogenous protein.

6. The tissue section selection method according to claim 1, wherein
in the embedded block-preparing step (a), the biological tissue fragment is immersed in a fixing solution for a predetermined period of time, before the biological tissue fragment and the standard substance are embedded in the embedding agent, and after the embedded tissue section preparing step (b), a fixing state determining step is performed, wherein said fixing state determining step comprises:

performing a staining treatment on the embedded tissue section, and determining a fixing state of the tissue section fixed with the fixing solution by comparing a light signal from an endogenous protein expressed in cells contained in the tissue section with a calibration curve as a reference, wherein the calibration curve represents a relationship between the predetermined period of time of the immersing and a color tone of the tissue section.

\* \* \* \* \*